(12) United States Patent
Smith

(10) Patent No.: US 11,564,893 B2
(45) Date of Patent: Jan. 31, 2023

(54) METHODS FOR PREPARING PARTICLES AND RELATED COMPOSITIONS

(71) Applicant: ModernaTX, Inc., Cambridge, MA (US)

(72) Inventor: Michael H. Smith, Needham, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 15/753,293

(22) PCT Filed: Aug. 17, 2016

(86) PCT No.: PCT/US2016/047406
§ 371 (c)(1),
(2) Date: Feb. 17, 2018

(87) PCT Pub. No.: WO2017/031232
PCT Pub. Date: Feb. 23, 2017

(65) Prior Publication Data
US 2018/0243230 A1   Aug. 30, 2018

Related U.S. Application Data

(60) Provisional application No. 62/206,121, filed on Aug. 17, 2015.

(51) Int. Cl.
*A61K 9/51* (2006.01)
*A61K 47/44* (2017.01)

(52) U.S. Cl.
CPC .......... *A61K 9/5192* (2013.01); *A61K 9/5146* (2013.01); *A61K 9/5176* (2013.01); *A61K 47/44* (2013.01)

(58) Field of Classification Search
CPC .... A61K 47/44; A61K 9/5146; A61K 9/5176; A61K 9/5192; G01N 11/08; H04L 43/062; H04L 43/0852; H04L 47/2416; H04L 47/26; H04L 47/283; H04L 47/41; H04L 65/80
See application file for complete search history.

(56) References Cited

U.S. PATENT DOCUMENTS

| | | | |
|---|---|---|---|
| 4,737,323 A | 4/1988 | Martin et al. | |
| 5,256,555 A | 10/1993 | Milburn et al. | |
| 5,853,990 A | 12/1998 | Winger et al. | |
| 6,303,378 B1 | 10/2001 | Bridenbaugh et al. | |
| 6,652,886 B2 | 11/2003 | Ahn et al. | |
| 7,371,404 B2 | 5/2008 | Panzner et al. | |
| 7,943,168 B2 | 5/2011 | Schlesinger et al. | |
| 8,058,069 B2 | 11/2011 | Yaworski et al. | |
| 8,158,601 B2 | 4/2012 | Chen et al. | |
| 8,568,784 B2 | 10/2013 | Lillard et al. | |
| 8,569,256 B2 | 10/2013 | Heyes et al. | |
| 8,580,297 B2 | 11/2013 | Essler et al. | |
| 8,618,240 B2 | 12/2013 | Podobinski et al. | |
| 8,642,076 B2 | 2/2014 | Manoharan et al. | |
| 8,663,599 B1 | 3/2014 | Sung et al. | |
| 8,691,750 B2 | 4/2014 | Constein et al. | |
| 8,703,204 B2 | 4/2014 | Bloom et al. | |
| 8,710,200 B2 | 4/2014 | Schrum et al. | |
| 8,754,062 B2 | 6/2014 | De Fougerolles et al. | |
| 8,822,663 B2 | 9/2014 | Schrum et al. | |
| 8,999,380 B2 | 4/2015 | Bancel et al. | |
| 9,221,891 B2 | 12/2015 | Bancel et al. | |
| 9,283,287 B2 | 3/2016 | Bancel et al. | |
| 9,303,079 B2 | 4/2016 | Bancel et al. | |
| 9,464,124 B2 | 10/2016 | Bancel et al. | |
| 9,512,456 B2 | 12/2016 | Wang et al. | |
| 9,533,047 B2 | 1/2017 | de Fougerolles et al. | |
| 9,597,380 B2 | 3/2017 | Chakraborty et al. | |

(Continued)

FOREIGN PATENT DOCUMENTS

| EP | 3452101 A2 | 3/2019 |
|---|---|---|
| WO | WO 2005/121348 A1 | 12/2005 |

(Continued)

OTHER PUBLICATIONS

Andreakos, E. et al., "Amphoteric Liposome Enable Systemic Antigen-Presenting Cell-Directed Delivery of CD40 Antisense and are Therapeutically Effective in Experimental Arthritis" Arthritis & Rheumatism, 2009, vol. 60, pp. 994-1005. (Year: 2009).*
International Search Report and Written Opinion for Application No. PCT/US2016/047406, dated Oct. 31, 2016.
Andreakos et al., Amphoteric liposomes enable systemic antigen-presenting cell-directed delivery of CD40 antisense and are therapeutically effective in experimental arthritis. Arthritis Rheum. Apr. 2009;60(4):994-1005. doi: 10.1002/art.24434.
Belliveau et al., Microfluidic synthesis of highly potent limit-size lipid nanoparticles for in vivo delivery of siRNA. Mol Ther Nucleic Acids. Aug. 2012; 1(8): e37.
Bose et al., Influence of cationic lipid concentration on properties of lipid-polymer hybrid nanospheres for gene delivery. Int J Nanomedicine. Sep. 2, 2015;10:5367-82. doi: 10.2147/IJN.S87120. eCollection 2015.
Gjetting et al., In vitro and in vivo effects of polyethylene glycol (PEG)-modified lipid in DOTAP/cholesterol-mediated gene transfection. Int J Nanomedicine. Aug. 9, 2010;5:371-83.

(Continued)

*Primary Examiner* — Janet L Epps-Smith
(74) *Attorney, Agent, or Firm* — Wolf, Greenfield & Sacks, P.C.

(57) ABSTRACT

Methods for preparing particles and related compositions are provided. In some embodiments, the particles include at least one polynucleotide (e.g., mRNA), and in certain embodiments, the particles may include at least one ionizable molecule (e.g., a lipid). A method for preparing a suspension including the particles may comprise one or more filtration steps. In some such embodiments, prior to or during filtration, one or more properties of the particles (e.g., surface charge) and/or one or more properties of the suspension (e.g., pH) may be altered. In some embodiments, altering one or more properties of the particles and/or suspension may improve yield, improve a characteristic of the resulting composition, and/or prevent or reduce certain problems, such as fouling during the filtration process.

32 Claims, 6 Drawing Sheets

(56) References Cited

U.S. PATENT DOCUMENTS

| | | |
|---|---|---|
| 9,868,691 B2 | 1/2018 | Benenato et al. |
| 9,872,900 B2 | 1/2018 | Ciaramella et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,207,010 B2 | 2/2019 | Besin et al. |
| 10,232,055 B2 | 3/2019 | Kariko et al. |
| 10,273,269 B2 | 4/2019 | Ciaramella |
| 10,286,086 B2 | 5/2019 | Roy et al. |
| 10,323,076 B2 | 6/2019 | Ellsworth et al. |
| 10,385,088 B2 | 8/2019 | Fraley et al. |
| 10,449,244 B2 | 10/2019 | Ciaramella et al. |
| 10,465,190 B1 | 11/2019 | Chen et al. |
| 10,493,143 B2 | 12/2019 | Ciaramella et al. |
| 10,526,629 B2 | 1/2020 | Rabideau et al. |
| 10,653,712 B2 | 5/2020 | Hoge |
| 10,653,767 B2 | 5/2020 | Ciaramella et al. |
| 10,695,419 B2 | 6/2020 | Ciaramella et al. |
| 10,857,105 B2 | 12/2020 | Benenato et al. |
| 10,925,958 B2 | 2/2021 | Ciaramella |
| 11,045,540 B2 | 6/2021 | Ciaramella |
| 11,103,578 B2 | 8/2021 | Ciaramella et al. |
| 11,351,242 B1 | 6/2022 | Lori et al. |
| 11,384,352 B2 | 7/2022 | Miracco |
| 11,406,703 B2 | 8/2022 | Kramarczyk et al. |
| 2005/0287540 A1 | 12/2005 | Murphy et al. |
| 2006/0083780 A1 | 4/2006 | Heyes et al. |
| 2007/0252295 A1 | 11/2007 | Panzner et al. |
| 2009/0042825 A1 | 2/2009 | Matar et al. |
| 2009/0042829 A1 | 2/2009 | Matar et al. |
| 2010/0112042 A1* | 5/2010 | Polisky ............... A61K 9/1271 514/1.1 |
| 2010/0130588 A1 | 5/2010 | Yaworski et al. |
| 2010/0267806 A1* | 10/2010 | Bumcrot ............... A61K 31/44 514/44 A |
| 2011/0065095 A1 | 3/2011 | Kida et al. |
| 2011/0200582 A1 | 8/2011 | Baryza et al. |
| 2011/0244026 A1 | 10/2011 | Guild et al. |
| 2011/0256175 A1 | 10/2011 | Hope et al. |
| 2012/0021042 A1* | 1/2012 | Panzner ............... A61K 9/127 424/450 |
| 2012/0178702 A1 | 7/2012 | Huang |
| 2013/0065942 A1 | 3/2013 | Matar et al. |
| 2013/0090372 A1 | 4/2013 | Budzik et al. |
| 2013/0102034 A1 | 4/2013 | Schrum et al. |
| 2013/0115274 A1 | 5/2013 | Knopov et al. |
| 2013/0129785 A1 | 5/2013 | Manoharan et al. |
| 2013/0142876 A1 | 6/2013 | Howard et al. |
| 2013/0158021 A1 | 6/2013 | Dong et al. |
| 2013/0171241 A1 | 7/2013 | Geall |
| 2013/0183244 A1 | 7/2013 | Hanes et al. |
| 2013/0183372 A1 | 7/2013 | Schutt et al. |
| 2013/0183373 A1 | 7/2013 | Schutt et al. |
| 2013/0183375 A1 | 7/2013 | Schutt et al. |
| 2013/0195967 A1* | 8/2013 | Guild ............... A61K 9/1271 514/44 R |
| 2013/0202684 A1 | 8/2013 | Geall et al. |
| 2013/0236974 A1* | 9/2013 | de Fougerolles .... A61K 9/1272 435/455 |
| 2013/0245103 A1 | 9/2013 | de Fougerolles et al. |
| 2013/0259923 A1 | 10/2013 | Bancel et al. |
| 2013/0266640 A1 | 10/2013 | De Fougerolles et al. |
| 2013/0330401 A1 | 12/2013 | Payne et al. |
| 2014/0044772 A1 | 2/2014 | Maclachlan et al. |
| 2014/0113137 A1 | 4/2014 | Podobinski et al. |
| 2014/0141070 A1 | 5/2014 | Geall et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0206753 A1 | 7/2014 | Guild et al. |
| 2014/0328825 A1 | 11/2014 | Meis et al. |
| 2014/0378538 A1 | 12/2014 | Bancel |
| 2015/0051268 A1 | 2/2015 | Bancel et al. |
| 2015/0056253 A1 | 2/2015 | Bancel et al. |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2016/0024140 A1 | 1/2016 | Issa et al. |
| 2016/0024141 A1 | 1/2016 | Issa et al. |
| 2016/0151284 A1 | 1/2016 | Heyes et al. |
| 2016/0032273 A1 | 2/2016 | Shahrokh et al. |
| 2016/0038612 A1 | 2/2016 | Hoge et al. |
| 2016/0243221 A1 | 8/2016 | Hoge et al. |
| 2016/0317647 A1 | 11/2016 | Ciaramella et al. |
| 2017/0043037 A1 | 2/2017 | Kariko et al. |
| 2017/0202979 A1 | 7/2017 | Chakraborty et al. |
| 2017/0204152 A1 | 7/2017 | Nelson et al. |
| 2017/0239371 A1* | 8/2017 | Guild ............... A61K 38/1816 |
| 2017/0130255 A1 | 10/2017 | Wang et al. |
| 2018/0000953 A1 | 1/2018 | Almarsson et al. |
| 2018/0002393 A1 | 1/2018 | Bancel et al. |
| 2018/0214537 A1 | 8/2018 | Mutzke et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0318409 A1 | 11/2018 | Valiante et al. |
| 2018/0363019 A1 | 12/2018 | Hoge |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0085368 A1 | 3/2019 | Bancel et al. |
| 2019/0099481 A1 | 4/2019 | Ciaramella et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0314292 A1 | 10/2019 | Benenato et al. |
| 2019/0314493 A1 | 10/2019 | Ciaramella et al. |
| 2019/0336452 A1 | 11/2019 | Brader |
| 2019/0336595 A1 | 11/2019 | Ciaramella |
| 2019/0351040 A1 | 11/2019 | Valiante et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0069793 A1 | 3/2020 | Ciaramella |
| 2020/0069794 A1 | 3/2020 | Ciaramella et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129608 A1 | 4/2020 | Ciaramella et al. |
| 2020/0129615 A1 | 4/2020 | Ciaramella et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2021/0046173 A1 | 2/2021 | Ciaramella et al. |
| 2021/0163919 A1 | 6/2021 | Issa et al. |
| 2021/0187097 A1 | 6/2021 | Ciaramella et al. |
| 2021/0217484 A1 | 7/2021 | Giessel et al. |
| 2021/0228707 A1 | 7/2021 | Mektar et al. |
| 2021/0268086 A1 | 9/2021 | Zhong et al. |
| 2021/0309976 A1 | 10/2021 | Dousis et al. |
| 2022/0031631 A1 | 2/2022 | Almarsson et al. |
| 2022/0047518 A1 | 2/2022 | Hennessy et al. |
| 2022/0054653 A1 | 2/2022 | Martini et al. |
| 2022/0125899 A1 | 4/2022 | Ashburn et al. |

(56) References Cited

U.S. PATENT DOCUMENTS

| | | |
|---|---|---|
| 2022/0145381 A1 | 5/2022 | Elich et al. |
| 2022/0236253 A1 | 7/2022 | Hopson |
| 2022/0241399 A1 | 8/2022 | Lusso et al. |

FOREIGN PATENT DOCUMENTS

| | | |
|---|---|---|
| WO | WO 2008/103276 A2 | 8/2008 |
| WO | WO 2010/042877 A1 | 4/2010 |
| WO | WO 2011/140627 A1 | 11/2011 |
| WO | WO 2012/006378 A1 | 1/2012 |
| WO | WO 2013/059496 A1 | 4/2013 |
| WO | WO 2013/064911 A2 | 5/2013 |
| WO | WO 2013/086526 A1 | 6/2013 |
| WO | WO 2013/093648 A2 | 6/2013 |
| WO | WO 2014/008334 A1 | 1/2014 |
| WO | WO 2014/071379 A1 | 5/2014 |
| WO | WO 2014/204728 A1 | 12/2014 |
| WO | WO 2015/095346 A1 | 6/2015 |
| WO | WO 2016/164762 A1 | 10/2016 |
| WO | WO 2016/201377 A1 | 12/2016 |
| WO | WO 2017/011773 A2 | 1/2017 |
| WO | WO 2017/015457 A1 | 1/2017 |
| WO | WO 2017/066789 A1 | 4/2017 |
| WO | WO 2017/070601 A1 | 4/2017 |
| WO | WO 2017/075038 A1 | 5/2017 |
| WO | WO 2017/127750 A1 | 7/2017 |
| WO | WO 2017/191274 A2 | 11/2017 |
| WO | WO 2017/201333 A1 | 11/2017 |
| WO | WO 2018/157009 A1 | 8/2018 |
| WO | WO 2018/170245 A1 | 9/2018 |
| WO | WO 2018/170256 A1 | 9/2018 |
| WO | WO 2018/170260 A1 | 9/2018 |
| WO | WO 2018/187590 A2 | 10/2018 |
| WO | WO 2018/232355 A1 | 12/2018 |
| WO | WO 2018/232357 A1 | 12/2018 |
| WO | WO 2019/036670 A1 | 2/2019 |
| WO | WO 2019/036683 A1 | 2/2019 |
| WO | WO 2019/036685 A1 | 2/2019 |
| WO | WO 2019/103993 A1 | 5/2019 |
| WO | WO 2019/148101 A1 | 8/2019 |
| WO | WO 2020/006242 A1 | 1/2020 |
| WO | WO 2020/056370 A1 | 3/2020 |
| WO | WO 2020/061284 A1 | 3/2020 |
| WO | WO 2020/061295 A1 | 3/2020 |
| WO | WO 2020/061367 A1 | 3/2020 |
| WO | WO 2020/097291 A1 | 5/2020 |
| WO | WO 2020/172239 A1 | 8/2020 |
| WO | WO 2020/185811 A1 | 9/2020 |
| WO | WO 2020/190750 A1 | 9/2020 |
| WO | WO 2020/243561 A1 | 12/2020 |
| WO | WO 2021/132589 A1 | 1/2021 |
| WO | WO 2021/030533 A1 | 2/2021 |
| WO | WO 2021/050864 A1 | 3/2021 |
| WO | WO 2021/055811 A1 | 3/2021 |
| WO | WO 2021/155243 A1 | 8/2021 |
| WO | WO 2021/159040 A2 | 8/2021 |
| WO | WO 2021/159130 A2 | 8/2021 |
| WO | WO 2021/204175 A1 | 10/2021 |
| WO | WO 2021/211343 A1 | 10/2021 |
| WO | WO 2021/222304 A1 | 11/2021 |
| WO | WO 2021/231929 A1 | 11/2021 |
| WO | WO 2021/231963 A1 | 11/2021 |
| WO | WO 2021/237084 A1 | 11/2021 |
| WO | WO 2021/247817 A1 | 12/2021 |
| WO | WO 2022/067010 A1 | 3/2022 |
| WO | WO 2022/150717 A1 | 7/2022 |
| WO | WO 2022/155524 A1 | 7/2022 |
| WO | WO 2022/155530 A1 | 7/2022 |

OTHER PUBLICATIONS

Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.

Leung et al. Microfluidic Mixing: a General Method for Encapsulating Macromolecules in Lipid Nanoparticle Systems. J Phys Chem B. Jul. 16, 2015;119(28):8698-706. doi: 10.1021/acs.jpcb.5b02891. Epub Jul. 7, 2015.

Malone et al., Cationic liposome-mediated RNA transfection. Proc Natl Acad Sci U SA. Aug. 1989;86 (16):6077-81.

Shea et al., Synthesis, hybridization properties and antiviral activity of lipidoligodeoxynucleotide conjugates. Nucleic Acids Res.Jul. 11, 1990;18(13):3777-83.

Uzgun et al., PEGylation improves nanoparticle formation and transfection efficiency of messenger RNA. Pharm Res. Sep. 2011; 28(9); 2223-2232.

Zhigaltsev et al., Bottom-Up design and synthesis of limit size lipid nanoparticle systems with aqueous and triglyceride cores using millisecond microfluidic mixing. Langmuir. Feb. 21, 2012; 28(7): 3633-3640.

Zimmermann et al., Electrolyte and pH-stabilities of aqueous solid lipid nanoparticle (SLN™) dispersions in artificial gastrointestinal media. Eur J Pharm Biopharm. Sep. 2001;52(2):203-10.

Kingston, 'Preparation of poly (A)+ RNA', Current protocols in molecular biology. 1993, vol. 21, No. 1, pp. 4.51-4.5.3.

Ouranidis et al., Pharma 4.0 Continuous mRNA Drug Products Manufacturing. Pharmaceutics. Aug. 31, 2021;13(9):1371. doi: 10.3390/pharmaceutics13091371.

Zeng et al., Formulation and Delivery Technologies for mRNA Vaccines. Curr Top Microbiol Immunol. Jun. 2, 2020;10.1007/82_2020_217. doi: 10.1007/82_2020_217.

U.S. Appl. No. 17/204,801, filed Mar. 17, 2021, Ciaramella et al.
U.S. Appl. No. 16/898,268, filed Jun. 10, 2020, Ciaramella et al.
U.S. Appl. No. 17/411,896, filed Aug. 25, 2021, Kramarczyk et al.
U.S. Appl. No. 17/000,201, filed Aug. 21, 2020, Stewart-Jones et al.
U.S. Appl. No. 17/000,215, filed Aug. 21, 2020, Metkar et al.

Hope et al., Reduction of Liposome Size and Preparation of Unilamellar Vesicles by Extrusion Techniques. In: Liposome Technology. 1993. Gregoriadis et al., Ed. vol. 1:123.

Morrissey et al., Potent and persistent in vivo anti-HBV activity of chemically modified siRNAs. Nat Biotechnol. Aug. 2005;23(8):1002-7. doi: 10.1038/nbt1122. Epub Jul. 24, 2005.

U.S. Appl. No. 17/683,171, filed Feb. 28, 2022, Ciaramella et al.
U.S. Appl. No. 17/554,182, filed Dec. 17, 2021, Ciaramella et al.
U.S. Appl. No. 17/590,479, filed Feb. 1, 2022, Ciaramella et al.
U.S. Appl. No. 16/897,859, filed Jun. 10, 2020, Ciaramella et al.
U.S. Appl. No. 17/737,532, filed May 5, 2022, Ciaramella et al.
U.S. Appl. No. 17/583,674, filed Jan. 25, 2022, Besin et al.
U.S. Appl. No. 17/523,034, filed Nov. 10, 2021, Hoge et al.
U.S. Appl. No. 17/523,060, filed Nov. 10, 2021, Hoge et al.
U.S. Appl. No. 17/548,172, filed Dec. 10, 2021, Ciaramella et al.
U.S. Appl. No. 17/839,401, filed Jun. 13, 2022, Ciaramella et al.
U.S. Appl. No. 16/897,734, filed Jun. 10, 2020, Ciaramella et al.
U.S. Appl. No. 17/830,742, filed Jun. 2, 2022, Miracco.
U.S. Appl. No. 17/852,974, filed Jun. 29, 2022, Marquardt et al.
U.S. Appl. No. 17/127,949, filed Dec. 18, 2020, Ciaramella.
U.S. Appl. No. 17/385,655, filed Jul. 26, 2021, Ciaramella et al.
U.S. Appl. No. 17/350,662, filed Jun. 17, 2021, Rabideau et al.
U.S. Appl. No. 17/245,973, filed Apr. 30, 2021, Ciaramella.
U.S. Appl. No. 17/155,592, filed Jan. 22, 2021, Ciaramella et al.
U.S. Appl. No. 16/765,285, filed May 19, 2020, Ciaramella et al.
U.S. Appl. No. 17/531,211, filed Nov. 19, 2021, Ciaramella et al.
U.S. Appl. No. 16/965,589, filed Jul. 28, 2020, Ciaramella et al.
U.S. Appl. No. 17/255,949, filed Dec. 23, 2020, Zhong et al.
U.S. Appl. No. 17/277,423, filed Mar. 18, 2021, Almarsson et al.
U.S. Appl. No. 17/277,452, filed Mar. 18, 2021, Hennessy et al.
U.S. Appl. No. 17/276,112, filed Mar. 12, 2021, Martini et al.
U.S. Appl. No. 17/438,049, filed Sep. 10, 2021, Elich et al.
U.S. Appl. No. 17/634,939, filed Feb. 11, 2022, Shamashkin et al.
U.S. Appl. No. 17/291,947, filed May 6, 2021, Ashburn et al.
U.S. Appl. No. 17/439,198, filed Sep. 14, 2021, Lusso et al.
U.S. Appl. No. 17/325,883, filed May 20, 2021, Dousis et al.
U.S. Appl. No. 17/816,696, filed Aug. 1, 2022, Dousis et al.
U.S. Appl. No. 17/737,581, filed May 5, 2022, Panther et al.
U.S. Appl. No. 17/761,420, filed Mar. 17, 2022, Amato et al.
U.S. Appl. No. 17/145,164, filed Jan. 8, 2021, Giessel et al.
U.S. Appl. No. 17/615,202, filed Nov. 30, 2021, Hopson.

(56) References Cited

OTHER PUBLICATIONS

U.S. Appl. No. 17/641,967, filed Mar. 10, 2022, John et al.
U.S. Appl. No. 17/840,478, filed Jun. 14, 2022, Kramarczyk et al.
U.S. Appl. No. 17/796,401, filed Jul. 29, 2022, Shaw et al.
U.S. Appl. No. 17/518,542, filed Nov. 3, 2021, Metkar et al.
U.S. Appl. No. 17/796,208, filed Jul. 28, 2022, Stewart-Jones et al.
U.S. Appl. No. 17/572,465, filed Jan. 10, 2022, Nachbagauer et al.
U.S. Appl. No. 17/726,971, filed Apr. 22, 2022, Hennessy.
U.S. Appl. No. 16/036,318, filed Jul. 16, 2018, Ciaramella et al.
U.S. Appl. No. 16/048,154, filed Jul. 27, 2018, Ciaramella et al.
U.S. Appl. No. 16/144,394, filed Sep. 27, 2018, Ciaramella et al.
U.S. Appl. No. 90/014,395, filed Oct. 24, 2019, Ciaramella et al.
U.S. Appl. No. 15/748,773, filed Jan. 30, 2018, Ciaramella et al.
U.S. Appl. No. 15/753,297, filed Feb. 17, 2018, Thompson.
U.S. Appl. No. 15/748,782, filed Jan. 30, 2018, Mousavi et al.
U.S. Appl. No. 15/767,587, filed Apr. 11, 2018, Ciaramella.
U.S. Appl. No. 16/450,882, filed Jun. 24, 2019, Ciaramella.
U.S. Appl. No. 16/833,409, filed Mar. 27, 2020, Ciaramella.
U.S. Appl. No. 15/767,600, filed Apr. 11, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 16/136,503, filed Sep. 20, 2018, Ciaramella et al.
U.S. Appl. No. 16/853,973, filed Apr. 21, 2020, Ciaramella et al.
U.S. Appl. No. 16/850,519, filed Apr. 16, 2020, Ciaramella et al.
U.S. Appl. No. 15/746,286, filed Jan. 19, 2018, Ciaramella et al.
U.S. Appl. No. 16/009,880, filed Jun. 15, 2018, Ciaramella et al.
U.S. Appl. No. 15/981,762, filed May 16, 2018, Bancel et al.
U.S. Appl. No. 16/582,621, filed Sep. 25, 2019, Chen et al.
U.S. Appl. No. 16/599,661, filed Oct. 11, 2019, Besin et al.
U.S. Appl. No. 16/001,786, filed Jun. 6, 2018, Hoge et al.
U.S. Appl. No. 16/333,330, filed Mar. 14, 2019, Hoge et al.
U.S. Appl. No. 16/839,278, filed Apr. 3, 2020, Hoge et al.
U.S. Appl. No. 16/389,545, filed Apr. 19, 2019, Ciaramella et al.
U.S. Appl. No. 16/368,270, filed Mar. 28, 2019, Ciaramella et al.
U.S. Appl. No. 16/805,587, filed Feb. 28, 2020, Ciaramella et al.
U.S. Appl. No. 16/468,838, filed Jun. 12, 2019, Miracco.
U.S. Appl. No. 16/001,765, filed Jun. 6, 2018, Marquardt et al.
U.S. Appl. No. 16/348,943, filed May 10, 2019, Ciaramella.
U.S. Appl. No. 16/467,142, filed Jun. 6, 2019, Ciaramella et al.
U.S. Appl. No. 16/603,111, filed Oct. 4, 2019, Brito et al.
U.S. Appl. No. 16/482,844, filed Aug. 1, 2019, Valiante et al.
U.S. Appl. No. 16/496,135, filed Sep. 20, 2019, Narayanan et al.
U.S. Appl. No. 16/483,012, filed Aug. 1, 2019, Mauger et al.
U.S. Appl. No. 16/657,122, filed Oct. 18, 2019, Rabideau et al.
U.S. Appl. No. 16/362,366, filed Mar. 22, 2019, Ciaramella.
U.S. Appl. No. 16/493,986, filed Sep. 13, 2019, Ciaramella et al.
U.S. Appl. No. 16/494,130, filed Sep. 13, 2019, Ciaramella et al.
U.S. Appl. No. 16/494,103, filed Sep. 13, 2019, Ciaramella et al.
U.S. Appl. No. 16/494,162, filed Sep. 13, 2019, Ciaramella.
U.S. Appl. No. 16/494,988, filed Sep. 17, 2019, Ciaramella et al.
U.S. Appl. No. 16/639,265, filed Feb. 14, 2020, Issa et al.
U.S. Appl. No. 16/639,305, filed Feb. 14, 2020, Issa et al.
U.S. Appl. No. 16/302,607, filed Nov. 16, 2018, Benenato et al.
U.S. Appl. No. 16/623,069, filed Dec. 16, 2019, Hoge et al.
U.S. Appl. No. 16/639,403, filed Feb. 14, 2020, Hoge et al.
U.S. Appl. No. 16/131,793, filed Sep. 14, 2018, Ciaramella et al.
U.S. Appl. No. 16/848,318, filed Apr. 14, 2020, Ciaramella et al.
U.S. Appl. No. 16/608,451, filed Oct. 25, 2019, Ciaramella et al.
U.S. Appl. No. 16/788,182, filed Feb. 11, 2020, Panther et al.
U.S. Appl. No. 16/794,318, filed Feb. 19, 2020, Mauger et al.
PCT/US2016/047406, Oct. 31, 2016, International Search Report and Written Opinion.

* cited by examiner

METHODS FOR PREPARING PARTICLES AND RELATED COMPOSITIONS

RELATED APPLICATIONS

This application is a national stage filing under 35 U.S.C. § 371 of international application number PCT/US2016/047406, filed Aug. 17, 2016, which was published under PCT Article 21(2) in English, which claims priority under 35 U.S.C. § 119(e) to U.S. Provisional Application Ser. No. 62/206,121, filed Aug. 17, 2015, the contents of each of which are incorporated herein by reference in its entirety for all purposes.

FIELD OF INVENTION

The present embodiments relate generally to methods for preparing particles comprising polynucleotides and related compositions.

BACKGROUND

It is of great interest in the fields of therapeutics, diagnostics, reagents, and for biological assays to be able to control protein expression. Most methods rely upon regulation at the transcriptional level (e.g., from DNA to mRNA), but not at the translational level (e.g., from mRNA to protein). Although attempts have been made to control protein expression on the translational level, the low levels of translation, the immunogenicity of the molecules, and other delivery issues have hampered the development of mRNA as a therapeutic.

There remains a need in the art to be able to design, synthesize and deliver a nucleic acid, e.g., a ribonucleic acid (RNA) such as a messenger RNA (mRNA) encoding a peptide or polypeptide of interest inside a cell, whether in vitro, in vivo, in-situ, or ex vivo, such as to effect physiologic outcomes which are beneficial to the cell, tissue or organ and ultimately to an organism.

SUMMARY OF THE INVENTION

Methods for preparing particles comprising polynucleotides and related compositions associated therewith are provided. In some embodiments, the preparation involves one or more filtration steps. The subject matter of this application involves, in some cases, interrelated products, alternative solutions to a particular problem, and/or a plurality of different uses of structures and compositions.

In some embodiments, a series of methods are provided. In one embodiment, a method comprises changing a pH of a suspension comprising particles comprising mRNA and an ionizable molecule from a first pH to a second pH, wherein the second pH is greater than a pKa of the ionizable molecule, and filtering the suspension to produce a filtered suspension comprising at least a portion of the particles, wherein a coefficient of variation of a cross-sectional dimension of the particles in the filtered suspension is less than or equal to about 20%.

In another embodiment, a method comprises changing a pH of a suspension comprising particles comprising mRNA and an ionizable molecule from a first pH to a second pH, wherein the second pH is greater than a pKa of the ionizable molecule, and forming a composition comprising at least a portion of the particles, wherein a coefficient of variation of a cross-sectional dimension of the particles in the composition is less than or equal to about 20%.

In another embodiment, a method comprises changing an average zeta potential of a plurality of particles comprising mRNA in a suspension from a first zeta potential to a second zeta potential, wherein the second zeta potential is less than the first zeta potential, and filtering the suspension to produce a filtered suspension comprising at least a portion of the particles, wherein a weight percentage of mRNA in the particles in the filtered suspension is greater than or equal to about 50% and less than or equal to about 99%.

In another embodiment, a method comprises changing an average zeta potential of a plurality of particles comprising mRNA in a suspension from a first zeta potential to a second zeta potential, wherein the second zeta potential is less than the first zeta potential, and forming a composition comprising at least a portion of the particles, wherein a weight percentage of mRNA in the particles in the composition is greater than or equal to about 50% and less than or equal to about 99%.

In another embodiment, a method comprises changing an average zeta potential of a plurality of particles comprising polynucleotides having greater than or equal to 50 nucleotides in a suspension from a first zeta potential to a second zeta potential, wherein the second zeta potential is less than the first zeta potential, and filtering the suspension to produce a filtered suspension comprising at least a portion of the particles, wherein a weight percentage of mRNA in the particles in the filtered suspension is greater than or equal to about 50% and less than or equal to about 99%.

In another embodiment, a method comprises changing an average zeta potential of a plurality of particles comprising polynucleotides having greater than or equal to 50 nucleotides in a suspension from a first zeta potential to a second zeta potential, wherein the second zeta potential is less than the first zeta potential, and forming a composition comprising at least a portion of the particles, wherein a weight percentage of mRNA in the particles in the composition is greater than or equal to about 50% and less than or equal to about 99%.

In another embodiment, a method of filtering comprises filtering a suspension comprising particles comprising a polynucleotide and an ionizable molecule having a pKa less than the pH of the suspension, wherein the filtration step comprises a concentration step and a diafiltration step, and wherein the permeate flux throughout the diafiltration step is greater than or equal to about 20 L/m$^2$h when the transmembrane pressure is between about 1 psi and about 20 psi.

In another set of embodiments, compositions are provided. In one embodiment, a composition comprises a plurality of particles comprising mRNA, wherein an average cross-sectional dimension of the particles in the composition is less than or equal to about 150 nm, a coefficient of variation of a cross-sectional dimension of the particles in the composition is less than or equal to about 20%, and a weight percentage of mRNA in the particles is greater than or equal to about 50% and less than or equal to about 99%.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Methods for preparing particles and related compositions are provided. In some embodiments, the particles include at least one polynucleotide (e.g., mRNA), and in certain embodiments, the particles may include at least one ionizable molecule (e.g., a lipid). A method for preparing a suspension including the particles may comprise one or more filtration steps. In some such embodiments, prior to or during filtration, one or more properties of the particles (e.g., surface charge) and/or one or more properties of the suspension (e.g., pH) may be altered. For instance, the average surface charge and/or zeta potential of the particles may be altered by changing the pH of a suspension containing the particles to a pH that is greater than or equal to the pKa of one or more components included in the particles (e.g., an ionizable molecule). In some such embodiments, the magnitude of the average surface charge and/or zeta potential of the particles after changing the pH is greater than the magnitude prior to changing the pH. In some embodiments, altering one or more properties of the particles and/or suspension may improve yield, improve a characteristic of the resulting composition, and/or prevent or reduce certain problems, such as fouling during the filtration process. For instance, the methods described herein may result in a composition including particles having less variations with respect to one or more therapeutically-relevant parameters (e.g., cross-sectional dimension, weight percentage of polynucleotide) compared to a composition formed by certain existing methods.

Figure 1:
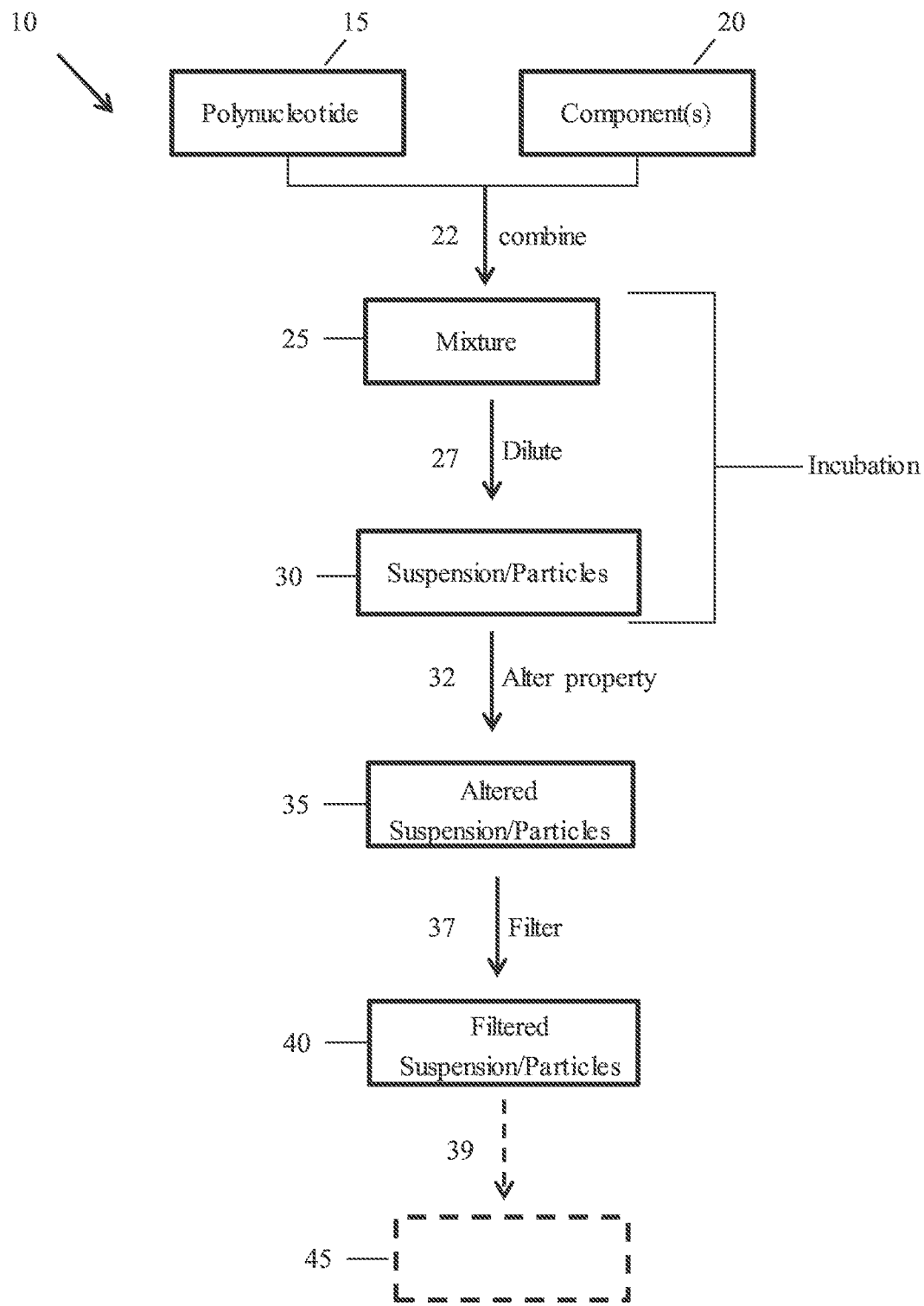
FIG. 1 is a process flow diagram showing a method of forming particles comprising polynucleotides, according to certain embodiments.

A non-limiting process flow diagram of a method for preparing a suspension including particles comprising polynucleotides (e.g., mRNA) is shown illustratively in FIG. 1. In some embodiments, a method 10 for preparing a suspension may include forming steps, an altering step, and/or one or more filtration steps, amongst others. For instance, a first solution 15 comprising polynucleotides (e.g., mRNA) and a second solution 20 comprising one or more components (e.g., ionizable molecule, sterol molecule) may be combined in step 22 to form a mixture 25 comprising the polynucleotides and component(s). After the combining step, the mixture may undergo an incubation step 27. In some embodiments, the incubation step may comprise one or more dilution steps. In some instances, a dilution step may be used to alter the concentration of one or more component (e.g., organic solvent) in the mixture. Over time, the polynucleotides and component(s) may spontaneously form, and/or be induced to form, a suspension containing particles 30. For example, the composition of the first and/or second solutions (e.g., solvents) may be selected to induce coprecipitation of the polynucleotides (e.g., mRNA) and one or more components (e.g., ionizable molecule) during an incubation step 27 to form particles 30.

In some embodiments, the incubation time, timing of dilution, ratio of the first and second solutions, and/or another condition (e.g., concentration of polynucleotides, pH) may be controlled to influence one or more properties of the resulting particles. For instance, the incubation time (i.e., the time allowed for the first and second solutions to mix or combine before a subsequent process step) may be controlled to influence the weight percentage of polynucleotide (e.g., mRNA) in the particles. In certain embodiments, the dilution timing may be controlled to tailor the average cross-sectional dimension of the particles. For instance, particle growth may be quenched after a certain period of time via a dilution. Methods for controlling the incubation time and other features are described in more detail below.

As shown illustratively in FIG. 1, the method may also involve altering one or more properties of the particles in a step 32 to form altered particles 35, as described in more detail below. Subsequently, the altered particles may be filtered during a filtering step 37 to form a filtered suspension containing particles 40.

Referring back to the step of forming the suspension containing particles 30, the particles may be formed by any suitable method. In some embodiments, the particle formation steps may be performed in a fluidic device, such as a microfluidic device. For instance, a first channel may contain a first solution and a second channel may contain a second solution. In some such embodiments, the combination step may be performed using a device comprising a T junction that merges the first and second channels, as described in U.S. Provisional Patent Application Ser. No. 62/040,989, filed Aug. 22, 2014, entitled "Lipid Nanoparticles for Nucleic Acid Molecules and Uses Thereof," which is incorporated by reference in its entirety.

Other methods of forming the particles described herein are also possible. For instance, in embodiments in which the particles are liposomes, methods of forming liposomes can be used as described in more detail below.

In some embodiments, the particles may be formed such that one or more of the components (e.g., initially contained in the second solution) at least partially (e.g., partially, completely) encapsulates at least a portion of the polynucleotides (e.g., initially contained in the first solution). For instance, in some embodiments, the particles comprise a component in the form of an ionizable molecule (e.g., an ionizable lipid). The ionizable molecules may encapsulate (e.g., partially, completely) at least a portion of the polynucleotides. In some cases, substantially all of the polynucleotides in the particles are encapsulated by the ionizable molecules. For example, the particles may include an outer layer of the ionizable molecules with the polynucleotides positioned in the interior of the particles. In other embodiments, a portion of the polynucleotides may be exposed at the surface of the particles, but another portion of the polynucleotides may be encapsulated within the interior of the particles. In certain embodiments, the particles comprise two or more components (e.g., an ionizable lipid, at least one other lipid, and/or at least one sterol) that together encapsulate (e.g., partially, completely) at least a portion of the polynucleotides. In some cases, substantially all of the polynucleotides in the particles are encapsulated by the two or more components. For instance, the polynucleotides may be encapsulated (e.g., partially, completely) by an ionizable lipid, at least one other lipid, and/or at least one sterol. A particle comprising polynucleotides and one or more lipid molecules may be referred to as a lipid particle.

In some embodiments, particles 30 may be formed such that one or more components of the particles may serve to at least partially (e.g., partially, completely) shield and/or neutralize the charge of the polynucleotides. In such cases, the magnitude of charge at the surface of the particles and/or the zeta potential of the particles may be relatively small. For instance, in embodiments in which the particles comprise an ionizable molecule, at least a portion of the charge of the polynucleotides may be shielded by the ionizable molecules. In some such embodiments, the ionizable molecule may be oppositely charged with respect to the overall charge of the polynucleotides.

In some embodiments, such particles having a relatively low surface charge may be difficult to filter (e.g., based on size) under certain conditions. For instance, passing the particles through a porous substrate to separate particles based on size and/or to remove certain contaminants may result in fouling of the porous substrate. In some such cases, fouling may limit the efficacy of separation, prevent the formation of a filtered suspension comprising particles that have a relatively narrow distribution in cross-sectional dimension, and/or allow a significant amount of certain contaminants to remain. In certain applications, such a variance in the cross-sectional dimension and/or concentration of certain contaminants may limit the utility of the particles. In some instances, the filtered suspension may have to undergo further complex, time-consuming, and/or costly all of y purification steps prior to utilization.

It has been discovered within the context of certain embodiments described herein that altering one or more properties of the particles and/or suspension prior to and/or during filtration, as indicated by step 32 in FIG. 1, can reduce and/or eliminate certain problems associated with filtration, such as fouling. In some embodiments, the altering step may increase the magnitude of the average surface charge and/or zeta potential of the particles. This change can increase the repulsion forces between the particles during filtration. Increasing the repulsion forces can reduce or prevent the agglomeration of substances (e.g., particles, components, and/or polynucleotides) at, near, or within the pores of the porous substrate, thereby reducing the amount of fouling of the porous substrate. In some instances, the altering step may allow efficacious sterile filtering of the suspension. In some instances, the altering step may allow efficacious tangential flow filtration, including ultrafiltration and diafiltration.

Additionally or alternatively, in some embodiments, altering one or more properties of the particles and/or suspension prior to and/or during filtration may allow the formation of particles 40 having a desirable property. For example, the particles may have a relatively small coefficient of variation (e.g., less than or equal to about 20%) in a cross-section dimension, a relatively high weight percentage of encapsulated polynucleotides (e.g., greater than or equal to about 85% of encapsulated/bound polynucleotide vs. free polynucleotide), amongst other features, as described in more detail herein.

It should be appreciated that the steps shown in FIG. 1 can vary. For example, although FIG. 1 shows the altering step 32 as being performed before filtration step 37, in some embodiments the altering step may occur during the filtration step as described herein. In other embodiments, the filtered suspension containing particles 40 may be subjected to one or more further processing steps 39 (e.g., altering tonicity, altering pH, altering stabilizer concentration, altering ionic strength) to obtain a suspension containing particles 45.

As described herein, a method for preparing a suspension including particles comprising polynucleotides (e.g., mRNA) may involve an altering step. In some embodiments in which the particles include an ionizable molecule, the altering step may involve changing a pH of the suspension from a first pH to a second pH that is greater than a pKa of the ionizable molecule. For instance, the pH of the suspension prior to an altering step (and/or during or after formation of the particles) may be less than a pKa of the ionizable molecule. The pH of the suspension may then be altered by adding a suitable base to increase the pH of the suspension to be greater than a pKa of the ionizable molecule.

In some embodiments, the pH of the suspension prior to an altering step (and/or during or after formation of the particles) may be less than or equal to about 6.5, less than or equal to about 6, less than or equal to about 5.8, less than or equal to about 5.5, less than or equal to about 5.2, less than or equal to about 5, less than or equal to about 4.8, or less than or equal to about 4.5. In some embodiments, the pH prior to the altering step (and/or during or after formation of the particles) may be greater than or equal to about 3, greater than or equal to about 3.2, greater than or equal to about 3.5, greater than or equal to about 3.8, greater than or equal to about 4.0, greater than or equal to about 4.2, greater than or equal to about 4.5, or greater than or equal to about 5.0. Combinations of the above referenced ranges are also possible (e.g., greater than or equal to about 3 and less than or equal to about 6). Other ranges are also possible. In some embodiments in which the pH is greater than the pKa prior to the altering step and/or during particle formation, one or more properties (e.g., weight percentage of polynucleotide, cross-sectional dimension, coefficient of variation in cross-sectional dimension) of the particle may be adversely affected or may make particle formation infeasible.

In some embodiments, the pH of the suspension after the altering step (e.g., a pH altering step) may be may be greater than or equal to about 6, greater than or equal to about 6.2, greater than or equal to about 6.4, greater than or equal to about 6.5, greater than or equal to about 6.6, greater than or equal to about 6.8, greater than or equal to about 7, greater than or equal to about 7.2, greater than or equal to about 7.4, greater than or equal to about 7.4, greater than or equal to about 7.5, greater than or equal to about 7.6, greater than or equal to about 7.8, or greater than or equal to about 8. In some embodiments, the pH after the altering step may be less than or equal to about 9.0, less than or equal to about 8.8, greater than or equal to about 8.6, less than or equal to about 8.5, greater than or equal to about 8.4, less than or equal to about 8.2, less than or equal to about 8.0, less than or equal to about 7.8, greater than or equal to about 7.6, or less than or equal to about 7.5. Combinations of the above referenced ranges are also possible (e.g., greater than or equal to 6.5 and less than or equal to about 8, greater than or equal to 7 and less than or equal to about 8). Other ranges are also possible.

In some embodiments, the pH of the suspension after the altering step (e.g., a pH altering step) may be within a certain range or may have a certain value greater than the pKa of one or more components (e.g., ionizable molecule) in the particles. In certain embodiments, the pH of the suspension after the altering step may be greater than or equal to about 0.2 pH units, greater than or equal to about 0.4 pH units, greater than or equal to about 0.5 pH units, greater than or equal to about 0.6 pH units, greater than or equal to about 0.8 pH units, greater than or equal to about 1 pH unit, greater than or equal to about 1.2 pH units, greater than or equal to about 1.4 pH units, or greater than or equal to about 1.5 pH units greater than the pKa of one or more components (e.g., ionizable molecule) in the particles. In some instances, the pH of the suspension after the altering step may be less than or equal to about 2.0 pH units, less than or equal to about 1.8 pH units, less than or equal to about 1.5 pH units, less than or equal to about 1.2 pH units, less than or equal to about 1.0 pH unit, or less than or equal to about 0.8 pH units greater than the pKa of one or more components (e.g., ionizable molecule) in the particles. Combinations of the above referenced ranges are also possible (e.g., greater than or equal to 0.5 pH units and less than or equal to about 2 pH units, greater than or equal to 1 pH unit and less than or equal to about 1.5 pH units). Other ranges are also possible. In some embodiments, the ionizable molecule is a cationic lipid such as 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-dimethylamino)butyanoyl)oxy)heptadecanedioate (L319). Other ionizable molecules are described herein.

In certain embodiments, the altering step may involve changing an average zeta potential of the particles from a first zeta potential to a second zeta potential that is greater than the magnitude of the first zeta potential.

In some embodiments, the average zeta potential of the particles prior to an altering step (and/or during or after formation of the particles) may be positive. In some such embodiments, the average zeta potential of the particles prior to an altering step (and/or during or after formation of the particles) may be greater than or equal to about +0.1 mV, greater than or equal to about +0.5 mV, greater than or equal to about +1.0 mV, greater than or equal to about +1.5 mV, greater than or equal to about +2.0 mV, greater than or equal to about +5.0 mV, greater than or equal to about +10.0 mV, greater than or equal to about +15.0 mV, greater than or equal to about +20.0 mV, or greater than or equal to about +25 mV. In some such cases, the average zeta potential of the particles prior to an altering step (and/or during or after formation of the particles) may be less than or equal to about +30 mV, less than or equal to about +25 mV, less than or equal to about +20 mV, less than or equal to about +15 mV, less than or equal to about +10 mV, less than or equal to about +5 mV, less than or equal to about +3 mV, or 0 mV. Combinations of the above-referenced ranges are also possible (e.g., greater than or equal to about +1.0 mV and less than or equal to about +30 mV).

In other embodiments, the average zeta potential of the particles prior to an altering step (and/or during or after formation of the particles) may be negative. In some such embodiments, the average zeta potential of the particles may be greater than or equal to about −2 mV, greater than or equal to about −1.8 mV, greater than or equal to about −1.5 mV, greater than or equal to about −1.2 m, greater than or equal to about −1 mV, greater than or equal to about −0.8 mV, or greater than or equal to about −0.5 mV. In some cases, the average zeta potential of the particles prior to an altering step (and/or during or after formation of the particles) may be 0 mV or less than or equal to 0.1 mV. Combinations of the above-referenced ranges are also possible (e.g., greater than or equal to about −2 mV and less than or equal to 0.1 mV).

In some embodiments, the average zeta potential of the particles after an altering step may be less than or equal to about −2 mV, less than or equal to about −3 mV, less than or equal to about −5 mV, less than or equal to about −8 mV, less than or equal to about −10 mV, less than or equal to about −12 mV, less than or equal to about −15 mV, greater than or equal to about −18 mV, less than or equal to about −20 mV, less than or equal to about −22 mV, less than or equal to about −25 mV, less than or equal to about −28 mV, less than or equal to about −30 mV, or less than or equal to about −35 mV. The average zeta potential of the particles after an altering step may be greater than or equal to about −40 mV, greater than or equal to about −38 mV, greater than or equal to about −35 mV, greater than or equal to about −30 mV, greater than or equal to about −28 mV, greater than or equal to about −25 mV, greater than or equal to about −22 mV, greater than or equal to about −20 mV, greater than or equal to about −18 mV, greater than or equal to about −15 mV, greater than or equal to about −12 mV, greater than or equal to about −10 mV, greater than or equal to about −8 mV. Combinations of the above referenced ranges are also possible (e.g., less than or equal to −1 mV and greater than or equal to about −10 mV). Other ranges are also possible.

In some embodiments, the average zeta potential of the particles may be negative after the altering step. In some such embodiments, the average zeta potential of the particles comprising an ionizable molecule and at least one polynucleotides may be less than the average zeta potential of essentially identical particle that do not comprise a polynucleotide. It should be understood that as used herein, when the zeta potential of particles are compared (e.g., less than, greater than), the comparison is based on the value of the zeta potential and not the magnitude. For instance, a zeta potential of −30 mV is less than a zeta potential of −1 mV.

Figure 2:
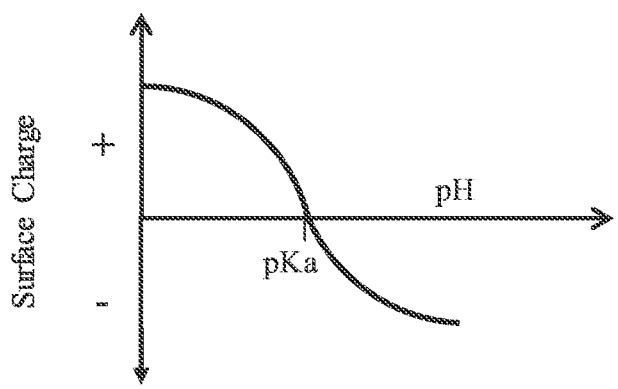
FIG. 2 is a schematic diagram of a graph showing the magnitude of charge of particles versus pH, according to certain embodiments.

In some instances, a change in pH of a suspension may cause a change in the magnitude and/or polarity of the surface charge, and accordingly the zeta potential, of the particles, as illustrated in FIG. 2. FIG. 2 illustratively shows the surface charge of particles in a suspension at a pH below the pKa of one or more components of the particles (e.g., an ionizable molecule) and at a pH above the pKa of one or more components of the particles. As illustrated in FIG. 2, the sign of the surface charge of the particles at a pH below the pKa may be opposite of the sign of the surface charge of the particles at a pH above the pKa. It should be understood that FIG. 2 is illustrative and that the sign of the surface charge of the particles need not be at a pH below the pKa need not be opposite of the sign of the surface charge of the particles at a pH above the pKa in all embodiments. In some embodiments, the average magnitude of the surface charge of the particles before the altering step may be greater than the magnitude the average magnitude of the surface charge of the particles after the altering step. In some such embodiments, the average magnitude of surface charge of the particles after the altering step may be greater than before the altering step. In certain embodiments, regardless of the average magnitude and/or polarity of the surface charge after the altering step, the altering step may serve to increase the repulsive force between particles.

Without being bound by theory, it is believed that the change in surface charge of the particles as a function of pH may be due, at least in part, to deprotonation of the ionizable lipid. For example, when the ionizable lipid is positively charged, at pH values less than the pKa, the positively charged ionizable lipid components bind negatively charged species on the surface and present an overall stoichiometric excess of positive charge. As the positive charge is diminished at pH values greater than the pKa, surface-accessible negatively charged groups (e.g., lipids, nucleotides) are no longer neutralized and can dominate the charge profile.

Figure 3:
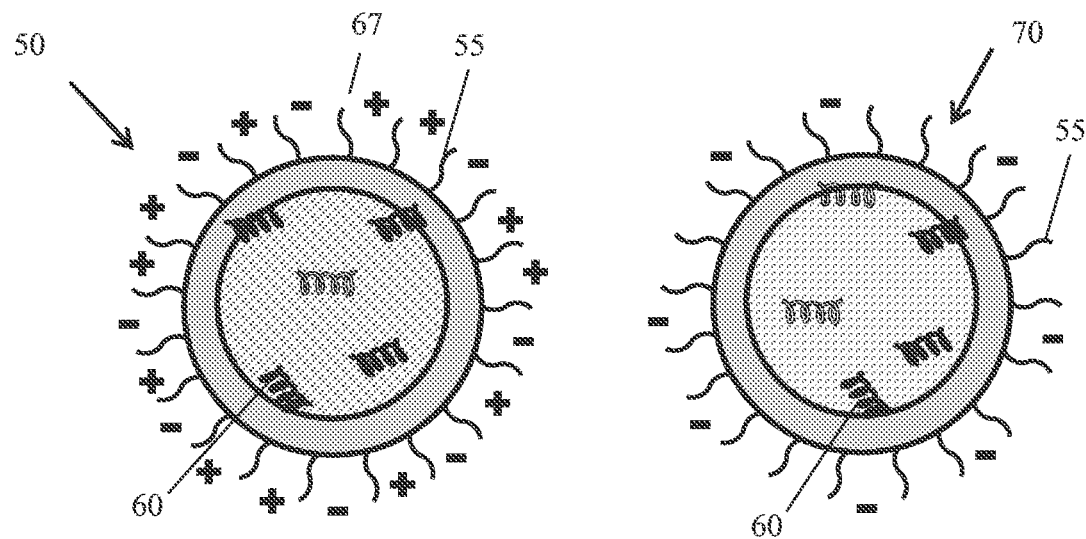
FIG. 3 is a schematic diagram of particles described herein, according to certain embodiments.

In some embodiments, and as shown illustratively in FIG. 3, after formation of a particle 50 and/or prior to an altering step, particle 50 may be arranged such that ionizable molecules 55 at least partially encapsulate polynucleotides 60. The ionizable molecule may comprise a charged portion (e.g., a nitrogen-containing functional group) that shields the charge of the polynucleotide, resulting in a relatively small charge at a surface 67 of the particle. Particle 50 may be present in a suspension, in some embodiments, prior to altering the pH of the suspension to a pH that is greater than the pKa of the ionizable molecule. In some embodiments, altering the pH of the suspension to a pH that is greater than the pKa of the ionizable molecule may alter the charge state of the charged portion of the ionizable molecule. For example, the percentage of charged ionizable molecules (e.g., ionizable lipids) may be reduced for positively charged ionizable molecules. In some embodiments, the change in the charge state of the charged portion of the ionizable molecule may result in reorganization of the particle components to form an altered particle 70. For example, as shown in FIG. 3, reorganization may result in at least a portion of the polynucleotides being present on the surface of particle 70. The presence of polynucleotides on the surface of the particle may increase the magnitude of the surface charge. For instance, the polynucleotides on the surface may make the particles have a greater surface charge. In other embodiments, the change in the charge state of the charged portion of the ionizable molecule may not result in structural reorganization of the particle. In some such embodiments, as the pH is adjusted and the charge state of ionizable molecule is diminished, the balance shifts resulting in a change in sign for zeta potential. In some such cases, the change in the ionization of charged groups on the surface of the particles results in a change in zeta potential by a shift in counter ion solvation around the molecules in the particle.

It should be understood that FIG. 3 is non-limiting and other particle configurations are possible. For instance, in some embodiments the ionizable molecules in particle 50 may have a different configuration compared to their configuration in particle 70. In some cases, particles 50 and 70 are liposomes (i.e., liposomal particles). In some such cases, the particles may comprise a lipid bilayer surrounding an aqueous interior. In some embodiments, liposomes can be, but not limited to, a multilamellar vesicle (MLV) and may contain a series of concentric bilayers separated by narrow aqueous compartments or an unicellular vesicle.

In some cases, particles including certain components may be more prone to fouling during filtration compared to particles including other components. In certain embodiments, particles prone to fouling may have a relatively low or neutral surface charge (e.g., particle 50 of FIG. 3). Causing the particles to rearrange to have an overall greater surface charge (e.g., particle 70 of FIG. 3) may reduce fouling as described in more detail herein.

In some embodiments, a method described herein comprises certain particle formation steps. In some such embodiments, the formation steps may comprise a combination step and/or an incubation step. The combination step may comprise mixing an aqueous solution comprising a buffer and polynucleotides (e.g., mRNA) (e.g., a first solution) with a solution comprising a solvent such as an organic solvent (e.g., an alcohol) and particle components (e.g., ionizable molecules, sterol) (e.g., a second solution). After the combination step, the suspension may be incubated to allow for particle formation. In some embodiments, one or more properties of the particles and/or resulting composition, such as weight percentage of polynucleotides (e.g., mRNA) in the particle, may be improved by tuning the incubation time. The incubation time may be measured from the time of combining the first and second solutions until the time of a subsequent process step (e.g., an alteration step). In some embodiments, the subsequent process step is altering the pH of the suspension to a pH greater than the pKa of a component (e.g., ionizable molecule) of the particles, such that the incubation time is measured from the time of combining the first and second solutions until the pH of the suspension is greater than the pKa a component of the particles.

An incubation time as described herein may vary. For instance, in some embodiments, the incubation time may be greater than or equal to about 3 minutes, greater than or equal to about 4 minutes, greater than or equal to about 5 minutes, greater than or equal to about 6 minutes, greater than or equal to about 8 minutes, greater than or equal to about 10 minutes, greater than or equal to about 12 minutes, or greater than or equal to about 15 minutes. In some embodiments, the incubation time may be less than or equal to about 30 minutes, less than or equal to about 20 minutes, less than or equal to about 18 minutes, less than or equal to about 15 minutes, less than or equal to about 12 minutes, less than or equal to about 10 minutes, less than or equal to about 8 minutes, or less than or equal to about 6 minutes. Combinations of the above referenced ranges are also possible (e.g., greater than or equal to 5 minutes and less than or equal to about 20 minutes). Other ranges are also possible.

In some embodiments, the incubation step may comprise one or more dilution steps (e.g., two dilution steps). In some embodiments, a dilution step may be used to alter the concentration of one or more components in the mixture (e.g., organic solvent). In some embodiments, the dilution step may facilitate particle formation. In certain embodiments, one or more dilution steps may adjust the pH of the mixture. In such embodiments, the pH of the mixture after the dilution step may be altered to be less than the pKa of one or more components (e.g., ionizable molecules) in the mixture.

In some embodiments, a dilution step may be used to slow down, limit, and/or quench particle growth. That is, in some embodiments, a dilution step may be used to control the average cross-sectional dimension of the particles. In certain embodiments, the incubation step may comprise two dilution steps. For instance, one dilution step may be used to change the concentration of a component in the mixture and another dilution step may be used to control (e.g., quench) particle growth.

As described herein, in some cases, an altering step (e.g., altering pH) may be performed. The altering step may be performed at any suitable time after one or more of the particle formation steps (e.g., a formation step, a combining step, an incubation step). For instance, in some embodiments, the time of an altering step may be greater than or equal to about 1 minute, greater than or equal to about 3 minutes, greater than or equal to about 5 minutes, greater than or equal to about 8 minutes, greater than or equal to about 10 minutes, greater than or equal to about 12 minutes, greater than or equal to about 15 minutes, greater than or equal to about 18 minutes, greater than or equal to about 20 minutes, or greater than or equal to about 25 minutes after one or more of the particle forming steps (e.g., a formation step, a combining step, an incubation step). In some embodiments, an altering step may be performed less than or equal to about 30 minute, less than or equal to about 28 minutes, less than or equal to about 25 minutes, less than or equal to about 22 minutes, less than or equal to about 20 minute, less than or equal to about 18 minutes, less than or equal to about 15 minutes, less than or equal to about 12 minutes, less than or equal to about 10 minutes, less than or equal to about 8 minutes, or less than or equal to about 6 minutes after one or more of the particle forming steps (e.g., a formation step, a combining step, an incubation step). Combinations of the above referenced ranges are also possible e.g., greater than or equal to 5 minutes and less than or equal to about 30 minutes).

In some embodiments, a method described herein may allow the particles to have a relatively high encapsulation efficiency of a component of the particle (e.g., a polynucleotide, sterol). For instance, in some embodiments, the encapsulation efficiency of a component may be greater than or equal to about 50%, greater than or equal to about 55%, greater than or equal to about 60%, greater than or equal to about 65%, greater than or equal to about 70%, greater than or equal to about 75%, greater than or equal to about 80%, greater than or equal to about 85%, greater than or equal to about 90%, greater than or equal to about 95%, or greater than or equal to about 99%. In some instances, the encapsulation efficiency of a component may be less than or equal to about 100%, less than or equal to about 99%, less than or equal to about 95%, less than or equal to about 90%, less than or equal to about 85%, less than or equal to about 80%, less than or equal to about 75%, less than or equal to about 70%, less than or equal to about 65%, or less than or equal to about 60%. Combinations of the above referenced ranges are also possible (e.g., greater than or equal to 75% and less than or equal to about 100%). The encapsulation efficiency is determined by the percentage (e.g., by weight, mol) of the component in the particles compared to the initial amount of the component used prior to particle formation and purification. In embodiments in which more than one component is included in the particles, each component may independently have an encapsulation efficiency in one or more of the above-referenced ranges.

As noted above, a method described herein may comprise one or more filtration steps. In some embodiments, the one or more filtration steps may include tangential flow filtration (e.g., cross-flow filtration with a membrane), clarifying filtration, and/or sterile filtration (e.g., with a 0.2 micron filter). In some embodiments, the methods steps described herein may prevent or reduce fouling during tangential flow filtration and/or sterile filtration. Other filtration methods are also possible, as described in more detail herein.

In some embodiments, the filtration step (e.g., tangential flow filtration) may include one or more concentration filtration steps and one or more diafiltration (e.g., buffer exchange, wash) steps. For instance, the filtration step may include two or more concentration filtration steps and a diafiltration step. In some such cases, a concentration step may be performed before and after the diafiltration step. As used herein, the term "concentration filtration step" has its ordinary meaning in the art and refers to a filtration step in which the concentration of one or more components in the collected fraction is greater than the concentration of component(s) in the original feed. In some embodiments, the collected fraction may be the permeate, also referred to as the filtrate. In some embodiments, the collected fraction is the retentate, also referred to as the concentrate. In some embodiments, the concentration filtration may be ultrafiltration. As used herein, the term "diafiltration" has its ordinary meaning in the art and refers to a technique that uses a filter to remove, replace, or lower the concentration of one or more components in the feed (e.g., salts, solvent). In some embodiments, a filtration step may include a diafiltration step that involves passing a certain volume (e.g., diafiltration volume) of a fluid through the filter and/or filtration system. As used herein, the term "diafiltration volume" or "diavolume" has its ordinary meaning in the art and may refer to the volume of retentate (e.g., total volume of reservoir plus the hold-up volume of tubing, filter, holder, etc.) at the start of diafiltration.

In some embodiments, multiple diafiltration volumes may be passed through the filter and/or filtration system during the filtration step. For instance, in some embodiments, greater than or equal to about one diafiltration volume, greater than or equal to about two diafiltration volumes, greater than or equal to about three diafiltration volumes, greater than or equal to about four diafiltration volumes, greater than or equal to about five diafiltration volumes, greater than or equal to about six diafiltration volumes, greater than or equal to about eight diafiltration volumes, greater than or equal to about ten diafiltration volumes, greater than or equal to about twelve diafiltration volumes, or greater than or equal to about fifteen diafiltration volumes may be used during a diafiltration step. In some instances, less than or equal to about twenty diafiltration volumes, less than or equal to about ten diafiltration volumes, less than or equal to about eight diafiltration volumes, less than or equal to about seven diafiltration volumes, less than or equal to about six diafiltration volumes, less than or equal to about five diafiltration volumes, less than or equal to about four diafiltration volumes, or less than or equal to about three diafiltration volumes may be used during a diafiltration step. Combinations of the above-referenced ranges are also possible (e.g., greater than or equal to about two diafiltration volumes and less than or equal to about ten diafiltration volumes, greater than or equal to about five diafiltration volumes and less than or equal to about eight diafiltration volumes).

As described herein, the disclosed method(s) may result in a reduction of fouling during filtration. In some embodiments, the reduction in fouling during filtration may allow a relatively high permeate flux to be achieved and/or may allow a relatively high permeate flux to be maintained throughout the filtration step or at least a portion of the filtration step (e.g., during a concentration step and/or diafiltration step). As used herein, the term "permeate flux" has its ordinary meaning in the art and refers to the rate of sample flow through a given filter area per unit time.

In some embodiments, the permeate flux during the filtration step and/or at least a portion of the filtration step (e.g., during concentration step(s) and/or a diafiltration step, e.g., after at least about 5 diafiltration volumes) at a transmembrane pressure of between about 1 psi and about 20 psi (e.g., between about 10 psi and about 15 psi) may be greater than or equal to about 10 L/m$^2$hr, greater than or equal to about 20 L/m$^2$hr, greater than or equal to about 30 L/m$^2$hr, greater than or equal to about 40 L/m$^2$hr, greater than or equal to about 50 L/m$^2$hr, greater than or equal to about 60 L/m$^2$hr, greater than or equal to about 70 L/m$^2$hr, greater than or equal to about 80 L/m$^2$hr, greater than or equal to about 90 L/m$^2$hr, greater than or equal to about 100 L/m$^2$hr, or greater than or equal to about 110 L/m$^2$hr. In some instances, the permeate flux during the filtration step and/or at least a portion of the filtration step (e.g., concentration step(s) and/or diafiltration step, e.g., after 5 diafiltration volumes) at a transmembrane pressure of between about 1 psi and about 20 psi (e.g., between about 10 psi and about 15 psi) may be less than or equal to about 120 L/m$^2$hr, less than or equal to about 110 L/m$^2$hr, less than or equal to about 100 L/m$^2$hr, less than or equal to about 90 L/m$^2$hr, less than or equal to about 80 L/m$^2$hr, less than or equal to about 70 L/m$^2$hr, less than or equal to about 60 L/m$^2$hr, less than or equal to about 50 L/m$^2$hr, less than or equal to about 40 L/m$^2$hr, less than or equal to about 30 L/m$^2$hr, or less than or equal to about 20 L/m$^2$hr. Combinations of the above-referenced ranges are also possible (e.g., greater than or equal to about 10 L/m$^2$hr and less than or equal to about 120 L/m$^2$hr, greater than or equal to about 20 L/m$^2$hr and less than or equal to about 110 L/m$^2$hr).

In some embodiments, the particles comprise one or more of ionizable molecules, polynucleotides, and optional components, such as sterols, neutral lipids, and a molecule capable of reducing particle aggregation (e.g., polyethylene glycol (PEG), polyethylene glycol-modified lipid).

In some embodiments, a particle described herein may include one or more ionizable molecules. The ionizable molecule may comprise a charged group and may have a certain pKa. In certain embodiments, the pKa of the ionizable molecule may be greater than or equal to about 6, greater than or equal to about 6.2, greater than or equal to about 6.5, greater than or equal to about 6.8, greater than or equal to about 7, greater than or equal to about 7.2, greater than or equal to about 7.5, greater than or equal to about 7.8, greater than or equal to about 8. In some embodiments, the pKa of the ionizable molecule may be less than or equal to about 10, less than or equal to about 9.8, less than or equal to about 9.5, less than or equal to about 9.2, less than or equal to about 9.0, less than or equal to about 8.8, or less than or equal to about 8.5. Combinations of the above referenced ranges are also possible (e.g., greater than or equal to 6 and less than or equal to about 8.5). Other ranges are also possible. In embodiments in which more than one type of ionizable molecules are present in a particle, each type of ionizable molecule may independently have a pKa in one or more of the ranges described above.

In general, an ionizable molecule comprises one or more charged groups. In some embodiments, an ionizable molecule may be positively charged or negatively charged. For instance, an ionizable molecule may be positively charged. For example, an ionizable molecule may comprise an amine group. As used herein, the term "ionizable molecule" has its ordinary meaning in the art and may refer to a molecule or matrix comprising one or more charged moiety. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidizolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule and/or matrix may be selected as desired.

In some cases, an ionizable molecule may include one or more precursor moieties that can be converted to charged moieties. For instance, the ionizable molecule may include a neutral moiety that can be hydrolyzed to form a charged moiety, such as those described above. As a non-limiting specific example, the molecule or matrix may include an amide, which can be hydrolyzed to form an amine, respectively. Those of ordinary skill in the art will be able to determine whether a given chemical moiety carries a formal electronic charge (for example, by inspection, pH titration, ionic conductivity measurements, etc.), and/or whether a given chemical moiety can be reacted (e.g., hydrolyzed) to form a chemical moiety that carries a formal electronic charge.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, an ionizable molecule is a lipid. For instance, the ionizable molecule may be a natural or synthetic lipid or lipid analog (i.e., lipophilic molecule). Non-limiting examples of natural or synthetic lipids or lipid analogs include fatty acyls, glycerolipids, glycerophospholipids, sphingolipids, saccharolipids and polyketides (derived from condensation of ketoacyl subunits), and sterol lipids and prenol lipids (derived from condensation of isoprene subunits). Other ionizable molecules are also possible.

In some embodiments, the ionizable molecule is a charged lipid. For instance, in some embodiments, the ionizable molecule is a cationic lipid. In one embodiment, the cationic lipid may have a positively charged hydrophilic head and a hydrophobic tail that are connected via a linker structure. Non-limiting examples of cationic lipids include C12-200, DLin-DMA (1,2-dilinoleyloxy-3-dimethylaminopropane), DLin-K-DMA, DODMA (1,2-dioleyloxy-N,N-dimethylaminopropane), DLin-MC3-DMA, DLin-KC2-DMA, 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625);

2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625), (20Z,23Z)—N,N-dimethylnonacosa-20,23-dien-10-amine, (17Z,20Z)—N,N-dimemylhexacosa-17,20-dien-9-amine, (1Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimethyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl] pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, (13Z,16Z)—N,N-dimethyl-3-nonyldocosa-13,16-dien-1-amine, N,N-dimethyl-1-[(1S,2R)-2-octylcyclopropyl] eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl]heptyl} dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy) propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl] ethyl}azetidine, (2S)-1-(hexyloxy)-N,N-dimethyl-3-[(9Z,12Z)-octadeca-9,12-dien-1-yloxyl]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy) propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoylo ctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-oc1ylcyclopropyl)octyl]oxy}-3-(octyloxy)propan-2-amine and (11E,20Z,23Z)—N,N-dimethylnonacosa-11,20,2-trien-10-amine, and pharmaceutically acceptable salts or stereoisomers thereof. In embodiments in which more than one type of ionizable molecules are present in a particle, each type of ionizable molecule may independently be chosen from the ionizable molecules described herein.

In some embodiments, an ionizable cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy)heptadecanedioate (L319), and pharmaceutically acceptable salts or stereoisomers thereof.

In some embodiments, the ionizable molecule comprises a nitrogen atom. In some such embodiments, a molar ratio of nitrogen atoms in the ionizable molecules to the phosphates in the polynucleotides (N:P ratio) may be greater than or equal to about 1:1, greater than or equal to about 2:1, greater than or equal to about 3:1, greater than or equal to about 5:1, greater than or equal to about 8:1, greater than or equal to about 10:1, greater than or equal to about 12:1, greater than or equal to about 15:1, or greater than or equal to about 20:1. In some embodiments, the N:P ratio may be less than or equal to about 20:1, less than or equal to about 18:1, less than or equal to about 15:1, less than or equal to about 12:1, less than or equal to about 10:1, less than or equal to about 8:1, or less than or equal to about 5:1 Combinations of the above referenced ranges are also possible (e.g., greater than or equal to 1:1 and less than or equal to about 20:1). Other ranges are also possible. In embodiments in which more than one type of ionizable molecules are present in a particle, each type of ionizable molecule may independently have a N:P ratio in one or more of the ranges described above.

In some embodiments, the ionizable molecule may be a lipid bound to a polycation. Non-limiting examples of polycations may include natural polycations (e.g., chitosan), synthetic polycations (e.g., polyamines, such as polyethylene imine) a cationic peptide or a polypeptide such as, but not limited to, polylysine, polyornithine and/or polyarginine.

The ionizable molecule may have any suitable molecular weight. In certain embodiments, the molecular weight of an ionizable molecule is less than or equal to about 2,500 g/mol, less than or equal to about 2,000 g/mol, less than or equal to about 1,500 g/mol, less than or equal to about 1,250 g/mol, less than or equal to about 1,000 g/mol, less than or equal to about 900 g/mol, less than or equal to about 800 g/mol, less than or equal to about 700 g/mol, less than or equal to about 600 g/mol, less than or equal to about 500 g/mol, less than or equal to about 400 g/mol, less than or equal to about 300 g/mol, less than or equal to about 200 g/mol, or less than or equal to about 100 g/mol. In some instances, the molecular weight of an ionizable molecule is greater than or equal to about 100 g/mol, greater than or equal to about 200 g/mol, greater than or equal to about 300 g/mol, greater than or equal to about 400 g/mol, greater than or equal to about 500 g/mol, greater than or equal to about 600 g/mol, greater than or equal to about 700 g/mol, greater than or equal to about 1000 g/mol, greater than or equal to about 1,250 g/mol, greater than or equal to about 1,500 g/mol, greater than or equal to about 1,750 g/mol, greater than or equal to about 2,000 g/mol, or greater than or equal to about 2,250 g/mol. Combinations of the above ranges (e.g., at least about 200 g/mol and less than or equal to about 2,500 g/mol) are also possible. In embodiments in which more than one type of ionizable molecules are present in a particle, each type of ionizable molecule may independently have a molecular weight in one or more of the ranges described above.

In some embodiments, the percentage (e.g., by weight, or by mole) of a single type of ionizable molecule and/or of all the ionizable molecules within a particle may be greater than or equal to about 30%, greater than or equal to about 35%, greater than or equal to about 40%, greater than or equal to about 42%, greater than or equal to about 45%, greater than or equal to about 48%, greater than or equal to about 50%, greater than or equal to about 52%, greater than or equal to about 55%, greater than or equal to about 58%, greater than or equal to about 60%, greater than or equal to about 62%, greater than or equal to about 65%, or greater than or equal to about 68%. In some instances, the percentage (e.g., by weight, or by mole) may be less than or equal to about 70%, less than or equal to about 68%, less than or equal to about 65%, less than or equal to about 62%, less than or equal to about 60%, less than or equal to about 58%, less than or equal to about 55%, less than or equal to about 52%, less than or equal to about 50%, or less than or equal to about 48%. Combinations of the above referenced ranges are also possible (e.g., greater than or equal to 30% and less than or equal to about 70%, greater than or equal to 40% and less than or equal to about 65%). In embodiments in which more than one type of ionizable molecules are present in a particle, each type of ionizable molecule may independently have a percentage (e.g., by weight, or by mole) in one or more of the ranges described above. The percentage (e.g., by weight, or by mole) may be determined by extracting the ionizable molecule(s) from the dried particles using, e.g., organic solvents, and measuring the quantity of the agent using high pressure liquid chromatography (i.e., HPLC), liquid chromatography-mass spectrometry, nuclear magnetic resonance, or mass spectrometry. Those of ordinary skill in the art would be knowledgeable of techniques to determine the quantity of a component using the above-referenced techniques. For example, HPLC may be used to quantify the amount of a component, by, e.g., comparing the area under the curve of a HPLC chromatogram to a standard curve.

As described herein, a particle may include a polynucleotide, i.e., a polymer of nucleotides. In some embodiments, a particle includes more than one (e.g., at least 2, 3, 4, 5, 6, etc. types of polynucleotides). Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5 bromouridine, C5 fluorouridine, C5 iodouridine, C5 methylcytidine, 7 deazaadenosine, 7 deazaguanosine, 8 oxoadenosine, 8 oxoguanosine, O(6) methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5' N phosphoramidite linkages). In some embodiments, the polynucleotide is mRNA, or alternative or modified mRNA. In some embodiments, the polynucleotide comprises at least about 50 nucleotides, at least about 100 nucleotides, at least about 250 nucleotides, at least about 500 nucleotides, at least about 750 nucleotides, at least about 1,000 nucleotides, at least about 1,500 nucleotides, at least about 2,000 nucleotides, at least about 2,500 nucleotides, at least about 3,000 nucleotides, at least about 3,500 nucleotides or at least about 4,000 nucleotides and less than about 10,000 nucleotides (e.g., between about 100 and about 5,000 nucleotides).

In some embodiments, the particle comprises one or more sterols (e.g., cholesterol). A non-limiting example of a sterol include cholesterol.

The sterol molecules may have any suitable molecular weight. In certain embodiments, the molecular weight of a sterol molecule may be less than or equal to about 2,500 g/mol, less than or equal to about 2,000 g/mol, less than or equal to about 1,500 g/mol, less than or equal to about 1,250 g/mol, less than or equal to about 1,000 g/mol, less than or equal to about 900 g/mol, less than or equal to about 800 g/mol, less than or equal to about 700 g/mol, less than or equal to about 600 g/mol, less than or equal to about 500 g/mol, less than or equal to about 400 g/mol, less than or equal to about 300 g/mol, less than or equal to about 200 g/mol, or less than or equal to about 100 g/mol. In some instances, the molecular weight of a sterol molecule may be greater than or equal to about 100 g/mol, greater than or equal to about 200 g/mol, greater than or equal to about 300 g/mol, greater than or equal to about 400 g/mol, greater than or equal to about 500 g/mol, greater than or equal to about 600 g/mol, greater than or equal to about 700 g/mol, greater than or equal to about 1000 g/mol, greater than or equal to about 1,250 g/mol, greater than or equal to about 1,500 g/mol, greater than or equal to about 1,750 g/mol, greater than or equal to about 2,000 g/mol, or greater than or equal to about 2,250 g/mol. Combinations of the above ranges (e.g., at least about 200 g/mol and less than or equal to about 2,500 g/mol) are also possible. In embodiments in which more than one type of sterol are present in a particle, each type of sterol may independently have a molecular weight in one or more of the ranges described above.

In some embodiments, the percentage (e.g., by weight, or by mole) of a single type of sterol (e.g., cholesterol) and/or of all the sterols in a particle may be greater than or equal to about 0.5%, greater than or equal to about 1%, greater than or equal to about 2%, greater than or equal to about 4%, greater than or equal to about 6%, greater than or equal to about 8%, greater than or equal to about 10%, greater than or equal to about 15%, greater than or equal to about 20%, greater than or equal to about 25%, greater than or equal to about 30%, greater than or equal to about 35%, greater than or equal to about 40%, greater than or equal to about 45%, or greater than or equal to about 50%. In some instances, the percentage (e.g., by weight, or by mole) may be less than or equal to about 60%, less than or equal to about 55%, less than or equal to about 50%, less than or equal to about 45%, less than or equal to about 40%, less than or equal to about 35%, less than or equal to about 30%, less than or equal to about 25%, less than or equal to about 20%, or less than or equal to about 15%. Combinations of the above referenced ranges are also possible (e.g., greater than or equal to 30% and less than or equal to about 60%). In embodiments in which more than one type of sterol are present in a particle, each type of sterol may independently have a percentage (e.g., by weight, or by mole) with respect to the particle in one or more of the ranges described above. The percentage (e.g., by weight, or by mole) may be determined as described above with respect to ionizable molecules.

In some embodiments, the particle comprises one or more neutral lipids (i.e., neutrally-charged lipids). Non-limiting examples of neutral lipids include DSPC, DPPC, POPC, DOPE and SM.

In some embodiments, a lipid described herein may be a cleavable lipid. Non-limiting examples of cleavable lipids include HGT4001, HGT4002, HGT4003, HGT4004 and/or HGT4005.

The neutral lipids may have any suitable molecular weight. In certain embodiments, the molecular weight of a neutral lipid may be less than or equal to about 2,500 g/mol, less than or equal to about 2,000 g/mol, less than or equal to about 1,500 g/mol, less than or equal to about 1,250 g/mol, less than or equal to about 1,000 g/mol, less than or equal to about 900 g/mol, less than or equal to about 800 g/mol, less than or equal to about 700 g/mol, less than or equal to about 600 g/mol, less than or equal to about 500 g/mol, less than or equal to about 400 g/mol, less than or equal to about 300 g/mol, less than or equal to about 200 g/mol, or less than or equal to about 100 g/mol. In some instances, the molecular weight of a neutral lipid may be greater than or equal to about 100 g/mol, greater than or equal to about 200 g/mol, greater than or equal to about 300 g/mol, greater than or equal to about 400 g/mol, greater than or equal to about 500 g/mol, greater than or equal to about 600 g/mol, greater than or equal to about 700 g/mol, greater than or equal to about 1000 g/mol, greater than or equal to about 1,250 g/mol, greater than or equal to about 1,500 g/mol, greater than or equal to about 1,750 g/mol, greater than or equal to about 2,000 g/mol, or greater than or equal to about 2,250 g/mol. Combinations of the above ranges (e.g., at least about 200 g/mol and less than or equal to about 2,500 g/mol) are also possible. In embodiments in which more than one type of neutral lipid are present in a particle, each type of neutral lipid may independently have a molecular weight in one or more of the ranges described above.

In some embodiments, the percentage (e.g., by weight, or by mole) of a single type of neutral lipid and/or of all the neutral lipids in a particle may be greater than or equal to about 0.5%, greater than or equal to about 1%, greater than or equal to about 2%, greater than or equal to about 4%, greater than or equal to about 6%, greater than or equal to about 8%, greater than or equal to about 10%, greater than or equal to about 15%, or greater than or equal to about 20%. In some instances, the percentage (e.g., by weight, or by mole) may be less than or equal to about 20%, less than or equal to about 18%, less than or equal to about 15%, less than or equal to about 412%, less than or equal to about 10%, less than or equal to about 8%, less than or equal to about 6%, less than or equal to about 5%, less than or equal to about 4%, or less than or equal to about 3%. Combinations of the above referenced ranges are also possible (e.g., greater than or equal to 0.5% and less than or equal to about 20%). The percentage (e.g., by weight, or by mole) may be determined as described above with respect to ionizable molecules. In embodiments in which more than one type of neutral lipid are present in a particle, each type of neutral lipid may independently have a percentage (e.g., by weight, or by mole) with respect to the particle in one or more of the ranges described above.

In some embodiments, the particle comprises one or more molecules capable of reducing particle aggregation. Non-limiting examples of molecules capable of reducing particle aggregation include PEG-distearoyl glycerol (PEG-DMG) (also referred herein as PEG-C14 or C14-PEG), PEG-cDMA, PEG-DSG (1,2-Distearoyl-sn-glycerol, methoxypolyethylene glycol), PEG-DMG (1,2-Dimyristoyl-sn-glycerol), and PEG-DPG (1,2-Dipalmitoyl-sn-glycerol, methoxypolyethylene glycol). Other molecules are also possible.

The molecule capable of reducing particle aggregation may have any suitable molecular weight. In certain embodiments, the molecular weight of a molecule capable of reducing particle aggregation may be less than or equal to about 2,500 g/mol, less than or equal to about 2,000 g/mol, less than or equal to about 1,500 g/mol, less than or equal to about 1,250 g/mol, less than or equal to about 1,000 g/mol, less than or equal to about 900 g/mol, less than or equal to about 800 g/mol, less than or equal to about 700 g/mol, less than or equal to about 600 g/mol, less than or equal to about 500 g/mol, less than or equal to about 400 g/mol, less than or equal to about 300 g/mol, less than or equal to about 200 g/mol, or less than or equal to about 100 g/mol. In some instances, the molecular weight of a molecule capable of reducing particle aggregation may be greater than or equal to about 100 g/mol, greater than or equal to about 200 g/mol, greater than or equal to about 300 g/mol, greater than or equal to about 400 g/mol, greater than or equal to about 500 g/mol, greater than or equal to about 600 g/mol, greater than or equal to about 700 g/mol, greater than or equal to about 1000 g/mol, greater than or equal to about 1,250 g/mol, greater than or equal to about 1,500 g/mol, greater than or equal to about 1,750 g/mol, greater than or equal to about 2,000 g/mol, or greater than or equal to about 2,250 g/mol. Combinations of the above ranges (e.g., at least about 200 g/mol and less than or equal to about 2,500 g/mol) are also possible. In embodiments in which more than one type of molecule capable of reducing particle aggregation are present in a particle, each type of molecule may independently have a molecular weight in one or more of the ranges described above.

In some embodiments, the percentage (e.g., by weight, or by mole) of a single type of molecule capable of reducing particle aggregation and/or of all the molecules capable of reducing particle aggregation in a particle may be greater than or equal to about 0.5%, greater than or equal to about 1%, greater than or equal to about 2%, greater than or equal to about 4%, greater than or equal to about 6%, greater than or equal to about 8%, greater than or equal to about 10%, greater than or equal to about 12%, greater than or equal to about 15%, or greater than or equal to about 18%. In some instances, the percentage (e.g., by weight, or by mole) may be less than or equal to about 20%, less than or equal to about 18%, less than or equal to about 15%, less than or equal to about 12%, less than or equal to about 10%, less than or equal to about 8%, less than or equal to about 7%, less than or equal to about 6%, less than or equal to about 5%, or less than or equal to about 4%. Combinations of the above referenced ranges are also possible (e.g., greater than or equal to 0.5% and less than or equal to about 7%, greater than or equal to 2% and less than or equal to about 20%). In embodiments in which more than one type of molecule capable of reducing particle aggregation are present in a particle, each type of molecule may independently have a percentage (e.g., by weight, or by mole) with respect to the particle in one or more of the ranges described above. The percentage (e.g., by weight, or by mole) may be determined as described above with respect to ionizable molecules.

In some embodiments, the particles may comprise a reactive component attached to dienophile as a chemically cleavable group which may provoking the release in vitro of the formulation and/or the polynucleotide.

In some embodiments, the particles may comprise a polymer, such as polyethylenimine (PEI), dithiobis(succinimidylpropionate) (DSP), Dimethyl-3,3'-dithiobispropionimidate (DTBP), poly(ethylene imine) biscarbamate (PEIC), poly(L-lysine) (PLL), histidine modified PLL, poly (N-vinylpyrrolidone) (PVP), poly(propylenimine (PPI), poly(amidoamine) (PAMAM), poly(amido ethylenimine) (SS-PAEI), triethylenetetramine (TETA), poly(β-aminoester), poly(4-hydroxy-L-proline ester) (PHP), poly(allylamine), poly(α-[4-aminobutyl]-L-glycolic acid (PAGA), Poly(D,L-lactic-co-glycolid acid (PLGA), Poly(N-ethyl-4-vinylpyridinium bromide), poly(phosphazene)s (PPZ), poly (phosphoester)s (PPE), poly(phosphoramidate)s (PPA), poly (N-2-hydroxypropylmethacrylamide) (pHPMA), poly(2-(dimethylamino)ethyl methacrylate) (pDMAEMA), poly(2-aminoethyl propylene phosphate) PPE_EA), chitsoan, galactosylated chitosan, N-dodecylated chitosan, histone, collagen or dextran-spermine, and combinations thereof. In one embodiment, the polymer may be an inert polymer such as, but not limited to, PEG. In one embodiment, the polymer may be a cationic polymer such as, but not limited to, PEI, PLL, TETA, poly(allylamine), Poly(N-ethyl-4-vinylpyridinium bromide), pHPMA and pDMAEMA. In one embodiment, the polymer may be a biodegradable PEI such as, but not limited to, DSP, DTBP and PEIC. In one embodiment, the polymer may be biodegradable such as, but not limited to, histine modified PLL, SS-PAEI, poly(β-aminoester), PHP, PAGA, PLGA, PPZ, PPE, PPA and PPE-EA.

In some embodiments, the particles described herein may be liposomes including one or more polynucleotides. In some cases, liposomes may encapsulate (e.g., partially, completely) the one or more polynucleotides.

In certain embodiments, a particle, formulation, or composition described herein has components and/or a configuration as described in International Pub. No. WO2013/090648, entitled "Modified nucleoside, nucleotide, and nucleic acid compositions", filed Dec. 14, 2012, and/or U.S. Pub. No. US2012/0295832, entitled "Novel Lipids and Compositions for Intracellular Delivery of Biologically Active Compounds", filed May 8, 2012, each of which is incorporated herein by reference in its entirety for all purposes.

In some embodiments, the ratio of one or more components (e.g., lipids, all other components) to polynucleotides (e.g., mRNA or alternative or modified mRNA alternative or modified mRNA) in the particles may be greater than or equal to about 5:1, greater than or equal to about 10:1, greater than or equal to about 15:1, greater than or equal to about 20:1, greater than or equal to about 25:1, greater than or equal to about 30:1, greater than or equal to about 35:1, greater than or equal to about 40:1, greater than or equal to about 45:1, greater than or equal to about 50:1, greater than or equal to about 55:1, or greater than or equal to about 60:1. In some embodiments, the ratio of one or more components to polynucleotides may be less than or equal to about 70:1, less than or equal to about 65:1, less than or equal to about 60:1, less than or equal to about 55:1, less than or equal to about 50:1, less than or equal to about 45:1, less than or equal to about 40:1, less than or equal to about 35:1, less than or equal to about 30:1, less than or equal to about 25:1, less than or equal to about 20:1, less than or equal to about 15:1, or less than or equal to about 10:1 Combinations of the above referenced ranges are also possible (e.g., greater than or equal to 1:1 and less than or equal to about 20:1). Other ranges are also possible.

In some embodiments, the particles comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a neutral lipid, a sterol and a molecule capable of reducing particle aggregation, for example a PEG or PEG-modified lipid.

In one set of embodiments, a particle formulation (e.g., lipid nanoparticle formulation) consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of about 20-60% cationic lipid:5-25% neutral lipid:25-55% sterol; 0.5-15% PEG-lipid.

In one set of embodiments, a formulation includes from about 25% to about 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., from about 35 to about 65%, from about 45 to about 65%, about 60%, about 57.5%, about 50% or about 40% on a molar basis.

In one set of embodiments, a formulation includes from about 0.5% to about 15% on a molar basis of a neutral lipid e.g., from about 3 to about 12%, from about 5 to about 10% or about 15%, about 10%, or about 7.5% on a molar basis. Exemplary neutral lipids include, but are not limited to, DSPC, POPC, DPPC, DOPE and SM. In one set of embodiments, the formulation includes from about 5% to about 50% on a molar basis of a sterol (e.g., about 15 to about 45%, about 20 to about 40%, about 40%, about 38.5%, about 35%, or about 31% on a molar basis. An exemplary sterol is cholesterol. In one set of embodiments, the formulation includes from about 0.5% to about 20% on a molar basis of the PEG or PEG-modified lipid (e.g., about 0.5 to about 10%, about 0.5 to about 5%, about 1.5%, about 0.5%, about 1.5%, about 3.5%, or about 5% on a molar basis. In one set of embodiments, the PEG or PEG modified lipid comprises a PEG molecule of an average molecular weight of 2,000 Da. In other embodiments, the PEG or PEG modified lipid comprises a PEG molecule of an average molecular weight of less than 2,000, for example around 1,500 Da, around 1,000 Da, or around 500 Da. Exemplary PEG-modified lipids include, but are not limited to, PEG-distearoyl glycerol (PEG-DMG) (also referred herein as PEG-C14 or C14-PEG), PEG-cDMA (further discussed in Reyes et al. *J. Controlled Release*, 107, 276-287 (2005).)

In one set of embodiments, a formulations includes 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-

DMA), and di((Z)-non-2-en-1-yl) 9-((4-(dimethylamino)butanoyl)oxy)heptadecanedioate (L319), 0.5-15% of a neutral lipid, 5-50% of a sterol, and 0.5-20% of a PEG or PEG-modified lipid on a molar basis.

In one set of embodiments, a formulation includes 35-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 3-12% of a neutral lipid, 15-45% of a sterol, and 0.5-10% of a PEG or PEG-modified lipid on a molar basis.

In one set of embodiments, a formulation includes 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 5-10% of a neutral lipid, 25-40% of a sterol, and 0.5-10% of a PEG or PEG-modified lipid on a molar basis.

In one set of embodiments, a formulation includes about 60% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.5% of a neutral lipid, about 31% of a sterol, and about 1.5% of a PEG or PEG-modified lipid on a molar basis.

In one set of embodiments, a formulation includes about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of a neutral lipid, about 38.5% of a sterol, and about 1.5% of a PEG or PEG-modified lipid on a molar basis.

In one set of embodiments, a formulation includes about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of a neutral lipid, about 35% of a sterol, about 4.5% or about 5% of a PEG or PEG-modified lipid, and about 0.5% of a targeting lipid on a molar basis. Non-limiting examples of a targeting lipid include lipids that are conjugated to a peptide, a small molecule, an antibody, an aptamer, and/or or fragment protein.

In one set of embodiments, a formulations includes about 40% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 15% of a neutral lipid, about 40% of a sterol, and about 5% of a PEG or PEG-modified lipid on a molar basis.

In one set of embodiments, a formulation includes about 57.2% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.1% of a neutral lipid, about 34.3% of a sterol, and about 1.4% of a PEG or PEG-modified lipid on a molar basis.

In one set of embodiments, a formulation includes about 57.5% of a cationic lipid selected from the PEG lipid is PEG-cDMA (PEG-cDMA is further discussed in Reyes et al.

(1. *Controlled Release*, 107, 276-287 (2005)), about 7.5% of a neutral lipid, about 31.5% of a sterol, and about 3.5% of a PEG or PEG-modified lipid on a molar basis.

In one set of embodiments, a formulation consists essentially of a lipid mixture in molar ratios of about 20-70% cationic lipid:5-45% neutral lipid:20-55% cholesterol:0.5-15% PEG-modified lipid. For instance, the formulation may have in a molar ratio of about 20-60% cationic lipid:5-25% neutral lipid:25-55% cholesterol:0.5-15% PEG-modified lipid. In some such cases, the formulation includes (DLin-KC2-DMA), dilinoleyl-methyl-4-dimethylaminobutyrate (DLin-MC3-DMA), DSPC, cholesterol, and PEG2000-DMG.

In particular embodiments, the molar lipid ratio is approximately 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Exemplary formulations (e.g., lipid nanoparticle compositions) and methods of making the same are described, for example, in Semple et al. (2010) *Nat. Biotechnol.* 28:172-176; Jayarama et al. (2012), *Angew. Chem. Int. Ed.*, 51: 8529-8533; and Maier et al. (2013) *Molecular Therapy* 21, 1570-1578 (each of which is incorporated herein by reference).

In some cases, the particles in the filtered suspension and/or the particles of a composition/formulation described herein may have a relatively narrow distribution in a cross-sectional dimension. For instance, in certain embodiments, the coefficient of variation of a cross-sectional dimension (e.g., diameter) of the particles in a suspension and/or composition/formulation may be less than or equal to about 30%, less than or equal to about 25%, less than or equal to about 20%, less than or equal to about 15%, less than or equal to about 10%, or less than or equal to about 5%. In certain embodiments, the coefficient of variation of a cross-sectional dimension (e.g., diameter) of the particles in a suspension and/or composition/formulation may be greater than or equal to about 1%, greater than or equal to about 3%, greater than or equal to about 5%, greater than or equal to about 7%, or greater than or equal to about 10%. Combinations of the above-referenced ranges are also possible (e.g., greater than or equal to about 1% and less than or equal to about 20%, greater than or equal to about 5% and less than or equal to about 20%).

In some embodiments, the particles in the filtered suspension and/or the particles of a composition/formulation described herein may have a relatively small average cross-sectional dimension (e.g., diameter). For instance, in some embodiments, the average cross-sectional dimension (e.g., average diameter) of the particles in a filtered suspension or composition/formulation may be less than or equal to about 1,000 nm, less than or equal to about 800 nm, less than or equal to about 600 nm, less than or equal to about 500 nm, less than or equal to about 400 nm, less than or equal to about 300 nm, less than or equal to about 200 nm, less than or equal to about 150 nm, less than or equal to about 120 nm, less than or equal to about 100 nm, or less than or equal to about 50 nm. In some embodiments, the average cross-sectional dimension (e.g., average diameter) of the particles in a filtered suspension or composition/formulation may be greater than or equal to about 10 nm, greater than or equal to about 50 nm, greater than or equal to about 70 nm, greater than or equal to about 100 nm, greater than or equal to about 200 nm, greater than or equal to about 300 nm, greater than or equal to about 400 nm, greater than or equal to about 500 nm, greater than or equal to about 600 nm, greater than or equal to about 700 nm, greater than or equal to about 800 nm, or greater than or equal to about 900 nm. combinations of the above-referenced ranges are also possible (e.g., greater than or equal to about 50 nm and less than or equal to about 200 nm, greater than or equal to about 70 nm and less than or equal to about 120 nm).

As used herein, the diameter of a particle for a non-spherical particle is the diameter of a perfect mathematical sphere having the same volume as the non-spherical particle. In general, the particles described herein are approximately spherical; however the particles are not necessarily spherical but may assume other shapes (e.g., discs, rods) as well.

In some embodiments, the particles are microparticles. In certain embodiments, the particles may have an average cross-sectional dimension of less than 1 mm. For instance, in some embodiments, the average cross-sectional dimension of the particles may be less than or equal to about 1,000 microns, less than or equal to about 500 microns, less than or equal to about 100 microns, less than or equal to about 50 microns, less than or equal to about 10 microns, or less than or equal to about 5 microns. In some embodiments, the average cross-sectional dimension of the particles may be greater than or equal to about 1 micron. Combinations of the above-referenced ranges are also possible.

In some embodiments, the particles are biocompatible. As used herein, the term "biocompatible" is intended to describe a material (e.g., particles, excipients) that is not toxic to cells. Particles are "biocompatible" if their addition to cells in vitro results in less than about 20% (e.g., less than about 15%, less than about 10%, less than about 5%, less than about 3%, less than about 2%, less than about 1%) cell death, and their administration in vivo does not substantially induce inflammation or other such adverse effects.

In some embodiments, the particles are biodegradable. As used herein, "biodegradable" compounds are those that, when introduced into cells, are broken down by the cellular machinery or by hydrolysis into components that the cells can either reuse or dispose of without significant toxic effects on the cells (i.e., less than about 20% (e.g., less than about 15%, less than about 10%, less than about 5%, less than about 3%, less than about 2%, less than about 1%) of the cells are killed when the components are added to cells in vitro). The components preferably do not induce inflammation or other adverse effects in vivo. In certain embodiments, the chemical reactions relied upon to break down the biodegradable compounds are uncatalyzed. For example, the inventive materials may be broken down in part by the hydrolysis of the polymeric material of the inventive coated particles.

In some embodiments, a method described herein may comprise adding an additional component to the particle. For instance, in some embodiments, a method may comprise attaching a surface modifying agent to the surface of the particle. In general, any suitable chemical compound can be attached to particle. Non-limiting examples of chemical compounds include small molecules, polynucleotides, proteins, peptides, metals, polymers, oligomers, organometallic complexes, lipids, carbohydrates, etc. The chemical compound may modify any property of particle including surface charge, hydrophilicity, hydrophobicity, zeta potential, size, etc. In certain embodiments, the chemical compound is a polymer such as polyethylene glycol (PEG). In certain embodiments, the chemical compound is a targeting moiety used to direct the particles to a particular cell, collection of cells, tissue, or organ system and/or to promote endocytosis or phagocytosis of the particle. Any targeting moiety known in the art of drug delivery may be used.

In some embodiments, the particles described herein may be made in a sterile environment.

In some embodiments, the particles may be created using microfluidic technology (see, e.g., Whitesides, George M., "The Origins and the Future of Microfluidics". Nature, 2006 442: 368-373; Stroock et al., "Chaotic Mixer for Micro-channels". Science, 2002 295: 647-651; and Valencia et al., "Microfluidic Platform for Combinatorial Synthesis and Optimization of Targeted Nanoparticles for Cancer Therapy". ACS Nano 2013 (DOI/101.1021/nn403370e). As a non-limiting example, controlled microfluidic formulation includes a passive method for mixing streams of steady pressure-driven flows in micro channels at a low Reynolds number as described, e.g., in Stroock et al., "Chaotic Mixer for Microchannels". Science, 2002 295: 647-651).

In one embodiment, the particles may be created using a micromixer chip such as, but not limited to, those from Harvard Apparatus (Holliston, Mass.) or Dolomite Microfluidics (Royston, UK). A micromixer chip can be used for rapid mixing of two or more fluid streams with a split and recombine mechanism.

In one embodiment, the particles may be created using NanoAssembler Y-mixer chip technology.

Particles formed via the methods described herein may be particularly useful for administering an agent to a subject in need thereof. In some embodiments, the particles are used to deliver a pharmaceutically active agent. In some instances, the particles are used to deliver a prophylactic agent. The particles may be administered in any way known in the art of drug delivery, for example, orally, parenterally, intravenously, intramuscularly, subcutaneously, intradermally, transdermally, intrathecally, submucosally, sublingually, rectally, vaginally, etc.

Once the particles have been prepared, they may be combined with pharmaceutically acceptable excipients to form a pharmaceutical composition. As would be appreciated by one of skill in this art, the excipients may be chosen based on the route of administration as described below, the agent being delivered, and the time course of delivery of the agent.

Pharmaceutical compositions described herein and for use in accordance with the embodiments described herein may include a pharmaceutically acceptable excipient. As used herein, the term "pharmaceutically acceptable excipient" means a non-toxic, inert solid, semi-solid or liquid filler, diluent, encapsulating material or formulation auxiliary of any type. Some examples of materials which can serve as pharmaceutically acceptable excipients are sugars such as lactose, glucose, and sucrose; starches such as corn starch and potato starch; cellulose and its derivatives such as sodium carboxymethyl cellulose, methylcellulose, hydroxypropylmethylcellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil;

corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen free water; isotonic saline; citric acid, acetate salts, Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups, and elixirs. In addition to the active ingredients (i.e., the particles), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3 butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, ethanol, U.S.P., and isotonic sodium chloride solution. In addition, sterile, fixed oils are conventionally employed as a solvent or suspending medium. For this purpose any bland fixed oil can be employed including synthetic mono or diglycerides. In addition, fatty acids such as oleic acid are used in the preparation of injectables.

The injectable formulations can be sterilized, for example, by filtration through a bacteria retaining filter, or by incorporating sterilizing agents in the form of sterile solid compositions which can be dissolved or dispersed in sterile water or other sterile injectable medium prior to use.

Compositions for rectal or vaginal administration may be suppositories which can be prepared by mixing the particles with suitable non irritating excipients or carriers such as cocoa butter, polyethylene glycol, or a suppository wax which are solid at ambient temperature but liquid at body temperature and therefore melt in the rectum or vaginal cavity and release the particles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also possible.

The ointments, pastes, creams, and gels may contain, in addition to the particles of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the particles of this invention, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the particles in a proper medium. Absorption enhancers can also be used to increase the flux of the compound across the skin. The rate can be controlled by either providing a rate controlling membrane or by dispersing the particles in a polymer matrix or gel.

Kits for use in preparing or administering the particles are also provided. A kit for forming particles may include any solvents, solutions, buffer agents, acids, bases, salts, targeting agent, etc. needed in the particle formation process. Different kits may be available for different targeting agents. In certain embodiments, the kit includes materials or reagents for purifying, sizing, and/or characterizing the resulting particles. The kit may also include instructions on how to use the materials in the kit. The one or more agents (e.g., pharmaceutically active agent) to be encapsulated in the particle are typically provided by the user of the kit.

Kits are also provided for using or administering the particles or pharmaceutical compositions thereof. The particles may be provided in convenient dosage units for administration to a subject. The kit may include multiple dosage units. For example, the kit may include 1-100 dosage units. In certain embodiments, the kit includes a week supply of dosage units, or a month supply of dosage units. In certain embodiments, the kit includes an even longer supply of dosage units. The kits may also include devices for administering the particles or a pharmaceutical composition thereof. Exemplary devices include syringes, spoons, measuring devices, etc. The kit may optionally include instructions for administering the particles (e.g., prescribing information).

"Composition": The terms "composition" and "formulation" are used interchangeably.

"Condition": As used herein, the terms "condition," "disease," and "disorder" are used interchangeably.

The following examples are intended to illustrate certain embodiments of the present invention, but do not exemplify the full scope of the invention.

EXAMPLES

Example 1

This example describes the effect of incubation time and pH on encapsulation efficiency of nanoparticles containing mRNA and an ionizable molecule (i.e., MC3 lipid). The particles also contained other lipids and a sterol and are referred to in the examples as lipid nanoparticles. Encapsulation percentages of greater than 90% were obtained under acidic conditions when incubations times were at least 300 seconds under acidic conditions.

Lipid nanoparticles were prepared using a micromixer channel in a T-configuration at sufficient flow rates to facilitate rapid mixing of an aqueous solution containing mRNA and an ethanol solution containing lipids. The mixing led to nano-precipitation and ultimately particle formation. The lipids used in this experiment were PEG-DMG (a diffusible PEG lipid which may impart physical stability to the lipid nanoparticle), cholesterol (e.g., which may provide structural support to the lipid nanoparticle), DSPC (a phospholipid known to be involved in lipid fusogenecity with the endosome compartment of a cell), and MC3 (an ionizable cationic lipid that becomes protonated in a low pH endosomal environment, which may lead to escape of the endosome compartment to the cytosol).

The ethanol solution was prepared by dissolving MC3, DSPC, cholesterol, and PEG-DMG at a mol % ratio of 50:10:38.5:1.5 in 200 proof ethanol to obtain a final lipid concentration of 12.5 mM. The stock ethanol solution was then filtered through a 0.8/0.2 micron filter. The ethanol solution was then stored at room temperature until use.

The aqueous solution contained about 0.2 mg/mL of mRNA in 20 mM sodium citrate pH 4.0. A tonicity modifier, sucrose, was added to adjust the total osmolarity of the solution. Once prepared, the aqueous solution was filtered through a 0.8/0.2 micron filter. The aqueous solution was then stored at room temperature until use.

Lipid nanoparticles were assembled by mixing the aqueous mRNA and lipid solutions using an impinging jet mixer in a Tee configuration. The flow ratios were offset between lipid and aqueous solutions, resulting in a total ethanol content at the site of mixing of 33%. The total cumulative flow rate of the aqueous and lipid solutions was 125 mL/min. The lipid nanoparticles produced were then diluted in-line at a 1:1 ratio with 20 mM sodium citrate pH 6.0 which was then followed by a second in-line dilution at 2:1 ratio with 1× citrate buffered saline (CBS). In this example, the first dilution was set at a cumulative flow rate of 125 mL/min followed by a second dilution at a cumulative flow rate of 250 mL/min. The particles were allowed to form for different incubation times. The incubation time was measured at the point at which the all of the components in the lipid and aqueous solutions were combined and ended with removal of the particles in this example.

Figure 4:
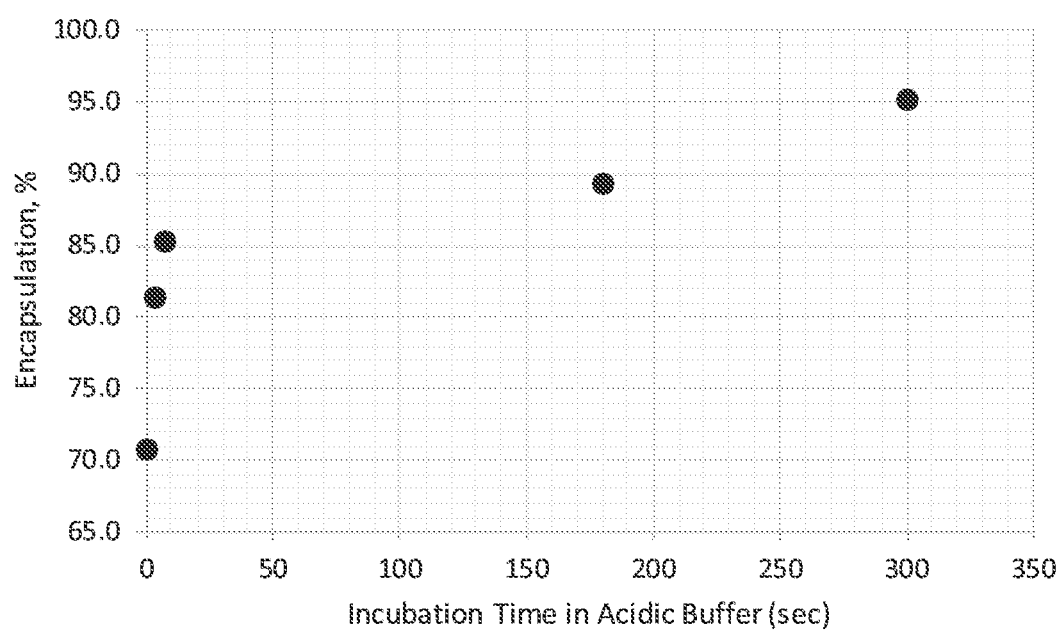
FIG. 4 shows a graph of percent encapsulation versus residence time in an acidic buffer, according to certain embodiments.

To investigate incubation times and the influence on percent encapsulation, the pH of the dilution buffers were adjusted to increase solution pH from less than about 6.5 to greater than about 7.0 at the site of dilution. The dilution time was modified by changing the length of tubing between the mixing Tee and the point of dilution, thus modulating the residence time within acidic buffer. Percent encapsulation was quantified by the Ribogreen fluorescence assay after buffer exchange into PBS via dialysis or TFF FIG. 4 shows a graph of percent encapsulation versus incubation time (also referred to as residence time) in the resulting acidic buffer (pH less than about 6.0) from the combination of the lipid and aqueous solutions. Encapsulation percentages of greater than 90% were achieved at 300 seconds as shown in FIG. 4.

Example 2

This example describes the change in surface charge of the nanoparticles associated with the altering step, which changes the pH of the suspension to a pH that is greater than the pKa of the ionizable molecule in the particles. This example shows that the surface charge of lipid nanoparticles containing ionizable lipid changed when the pH was altered to be greater than the pKa of the ionizable lipid. The magnitude of the change in surface charge was greater for lipid nanoparticles containing mRNA than for lipid nanoparticles that did not contain mRNA.

Figure 5:
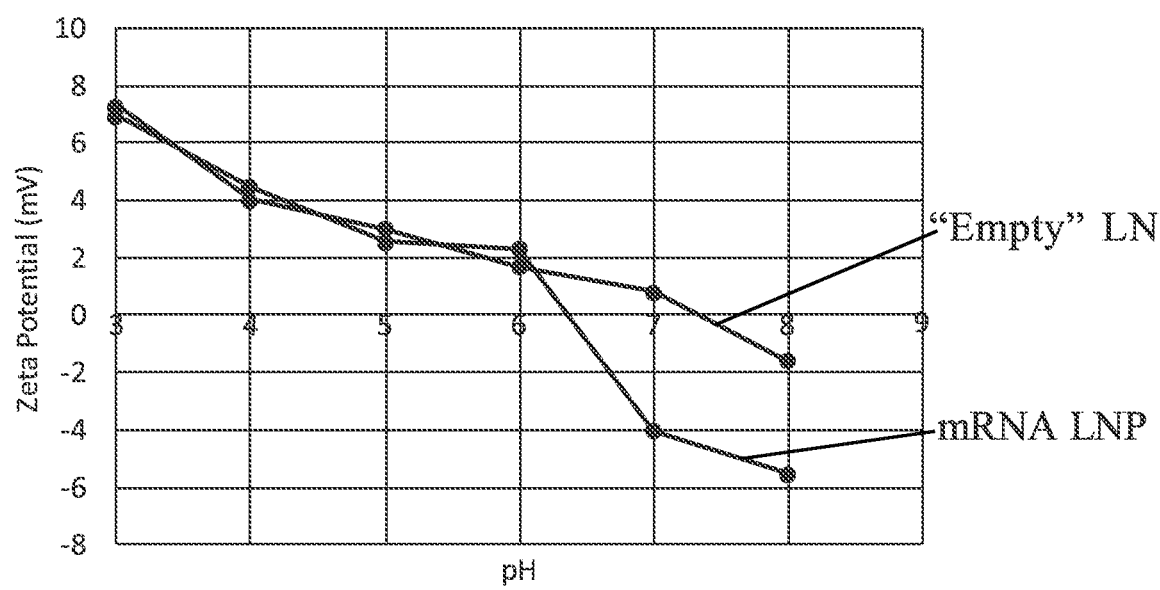
FIG. 5 shows a graph of zeta potential versus pH for various particles, according to certain embodiments.

Lipid nanoparticles containing mRNA were formed as described in Example 1. Lipid nanoparticles that did not contain mRNA ("Empty") were formed by a similar process as described in Example 1 except the aqueous solution did not contain mRNA. The ionizable lipid had a pKa of 6.3. After an incubation time of at least 300 seconds, the pH of the suspension containing the mRNA and the suspension containing the empty lipid nanoparticles was altered by changing the pH of the suspension. Particles were further purified by TFF and were subsequently filtered through a sterilizing-grade membrane. The zeta potential of the lipid particles were measured at various pHs of the resulting suspension using a Wyatt Mobius zeta-potentiometer. FIG. 5 shows a graph of zeta potential versus pH for mRNA and empty lipid nanoparticles. As shown in FIG. 5, the zeta potential of the empty and mRNA lipid nanoparticles are substantially the same until the isoelectric point of the ionizable lipid. After the isoelectric point, the surface charge of the mRNA lipid nanoparticles were substantially more negative than the empty nanoparticles.

Example 3

This example describes the filtration properties of suspensions containing mRNA lipid nanoparticles that have a pH greater than the pKa of the ionizable lipid in the particle. When the pH of the suspension was greater than the pKa of the ionizable lipid, the filtration time was reduced, a higher permeate flux was achieved throughout the filtration process, and the coefficient in variation of the resulting particles was reduced compared to a suspension having a pH less than the pKa of the ionizable lipid (control). Lipid nanoparticles containing mRNA were formed as described in Example 1.

The pKa of the ionizable lipid was 6.3. After formation of the particles and allowing the particles to incubate for at least 300 seconds, the pH of the suspension was changed from a pH of about 5.7 to a pH of about 7.4 in an altering step. The pH was altered by volumetric addition of a 1M Tris pH 8 buffer to a final buffer composition of 100 mM Tris. The control suspension was also incubated for at least 300 second but the pH of the suspension was not altered and remained at about pH 5.7 prior to diafiltration. However, pH 5.7 buffer was added to the control to ensure that the concentration of particles were substantially the same in both suspension. For the control, the pH of the suspension was changed gradually during filtration using diafiltration. The pH was increased during the diafiltration step with each diafiltration volume (DV) and a pH of 7.0 was reached after six diafiltration volumes. The pH at two DV and four DV were 6.05 and 6.41, respectively.

Figure 6A:
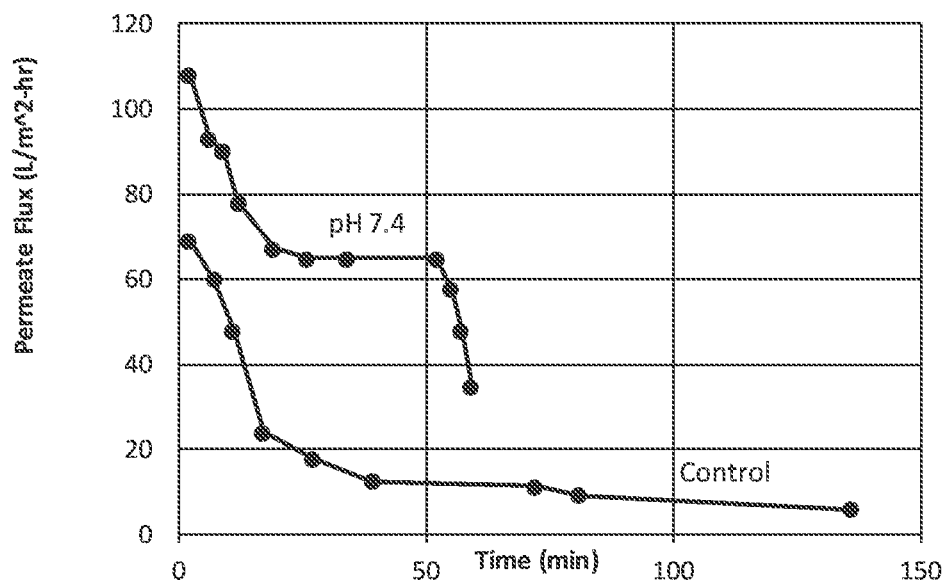
FIG. 6A shows a graph of permeate flux versus time for suspensions with various pHs, according to certain embodiments.
Figure 6B:
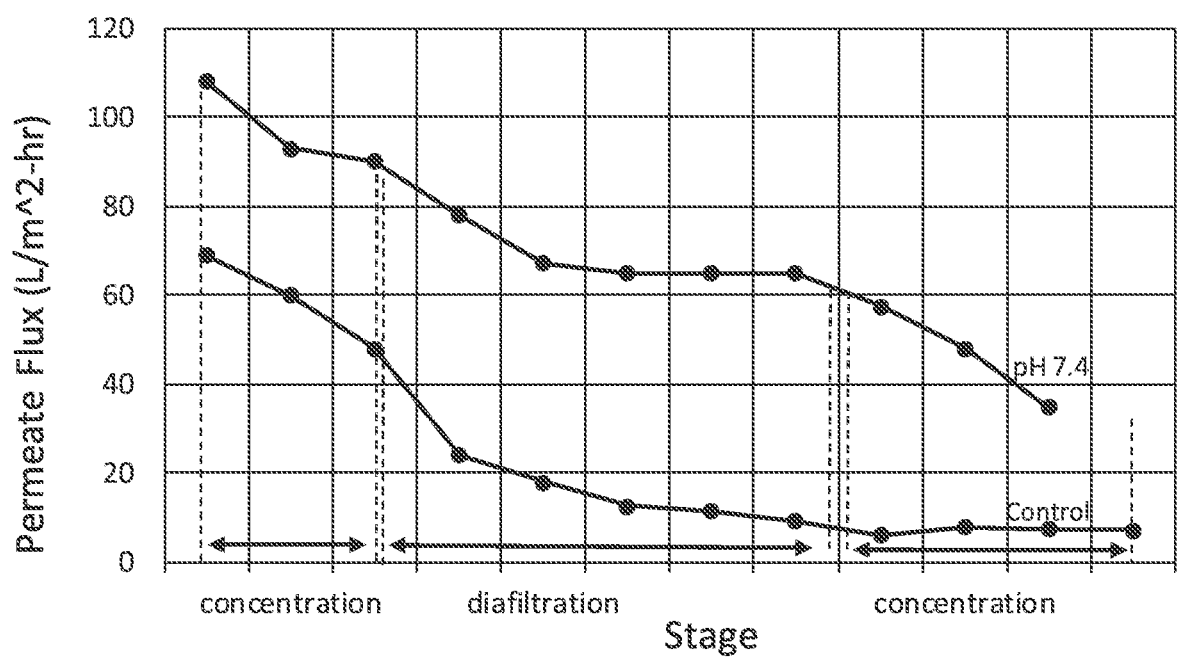
FIG. 6B shows a graph of permeate flux at different stages of tangential flow filtration for suspensions with various pHs, according to certain embodiments.

Both suspensions were filtered using tangential flow filtration. The tangential flow filtration process involved a first concentration step, then a diafiltration step using six diafiltration volumes, and a second concentration step. FIG. 6A shows the permeate flux versus time for the two suspensions. The suspension having a pH of about 7.4 had a filtration time of about 50 minutes while the suspension having a pH of about 5.7 has a filtration time of about 140 minutes. The filtration time included a first concentration step, diafiltration with 12 diafiltration volumes, and a final concentration step. The higher permeate flux achieved with the suspension having a pH of about 7.4 increased the filtration rate resulting in a lower filtration time. FIG. 6B shows the permeate flux at each stage of the tangential flow filtration for both suspensions. As shown in FIG. 6B, the permeate flux for the suspension having a pH of about 7.4 was greater than the suspension having a pH of about 5.7 during all stages of filtration. Thus, the suspension having a pH greater than the pKa of the ionizable lipid had better filtration performance than the suspension having a pH less than the pKa of the ionizable lipid.

Figure 7A:
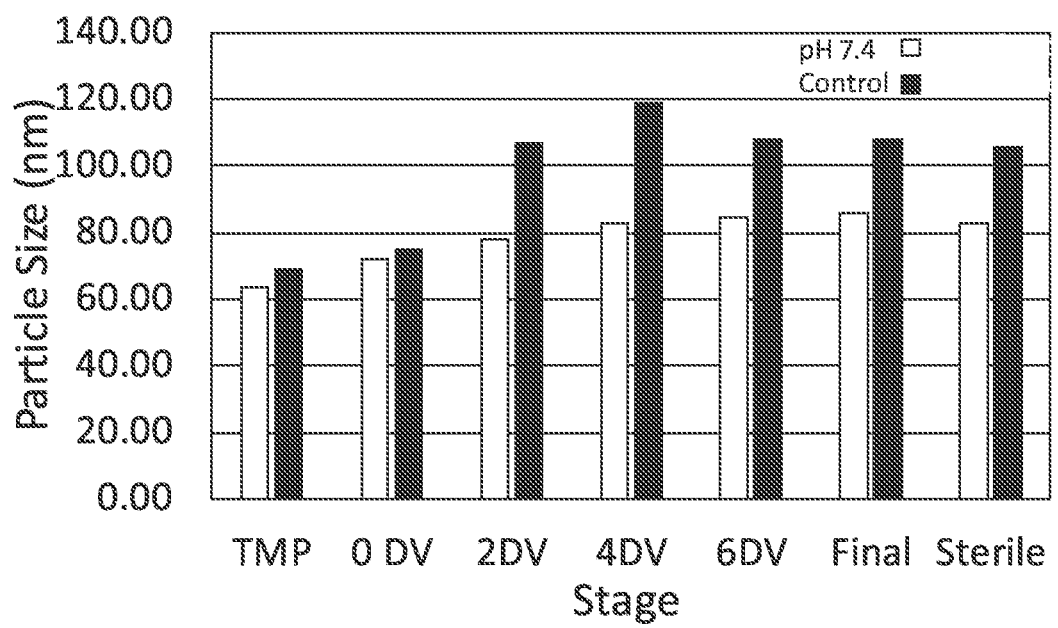
FIG. 7A shows the average particle size during various stages of tangential flow filtration and after a sterile filtration for suspensions with various pHs, according to certain embodiments.
Figure 7B:
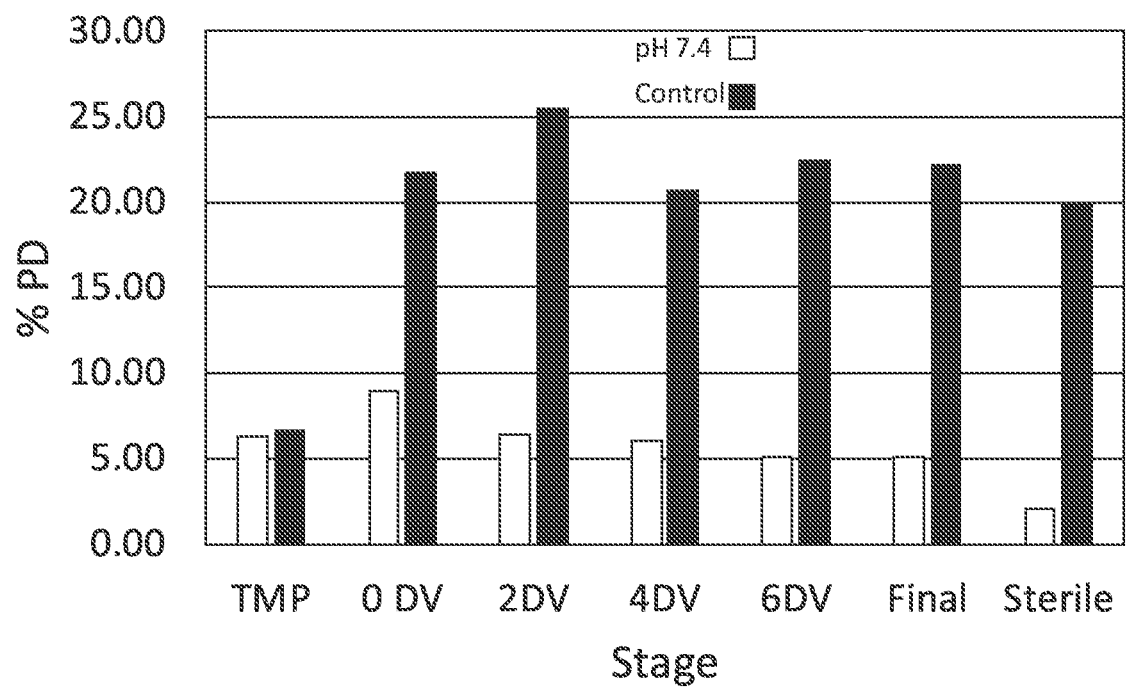
FIG. 7B shows the percent polydispersity for particles in suspensions with various pHs during various stages of tangential flow filtration and after a sterile filtration, according to certain embodiments.

The pH of the suspension during tangential flow filtration also influenced the average particle size, as well as polydispersity, of the filtered suspension. FIG. 7A shows the average particle size during various stages of tangential flow filtration (wherein DV stands for diafiltration volume), and after a sterile filtration for both suspensions. As shown in FIG. 7A, the average particle size of the particles in the suspension having a pH of about 7.4 was smaller than the average particle size of the particles in the suspension having a pH of about 5.7 after tangential flow filtration and sterile filtration. FIG. 7B shows the percent polydispersity for the particles during various stages of tangential flow filtration and after a sterile filtration for both suspensions. As shown in FIG. 7B, the suspension having a pH of about 7.4 had a significantly lower polydispersity in average particle size than the suspension having a pH of about 5.7. Notably, after sterile filtration, the pH 7.4 suspension had a polydispersity of less than about 3% and the pH 5.7 suspension had a polydispersity of about 20%.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method comprising:
changing a pH of a suspension comprising particles comprising mRNA comprising greater than or equal to 100 nucleotides and less than or equal to 10,000 nucleotides in length, and an ionizable molecule and a molecule capable of reducing particle aggregation from a first pH to a second pH, wherein the second pH is greater than a pKa of the ionizable molecule, wherein the pKa of the ionizable molecule is greater than or equal to about 6, wherein the molecule capable of reducing particle aggregation is a PEG lipid; and subsequently
filtering the suspension by tangential flow filtration (TFF) to produce a filtered suspension comprising at least a portion of the particles, wherein a coefficient of variation of a cross-sectional dimension of the particles in the filtered suspension is less than or equal to about 20%.

2. The method as in claim 1, wherein the filtering step comprises passing at least a portion of the suspension thorough a porous substrate.

3. The method as in claim 1, wherein the filtering step comprises passing the suspension through a filter having a mean pore size of less than or equal to about 0.2 microns after the tangential flow filtration.

4. The method as in claim 1, comprising forming the particles comprising mRNA and the ionizable molecule and the molecule capable of reducing particle aggregation.

5. The method as in claim 1, wherein the forming step comprises exposing a first solution comprising the ionizable molecule to a second solution comprising the mRNA to form the suspension comprising the particles.

6. The method as in claim 5, wherein the first solution comprises an organic solvent.

7. The method as in claim 6, wherein the organic solvent is an alcohol.

8. The method as in claim 5, wherein the second solution comprises an aqueous solution comprising a buffer.

9. The method as in claim 5, wherein the pH of the first solution is less than or equal to about pH 6.

10. The method as in claim 5, wherein the pH of the first solution is greater than about pH 6.

11. The method as in claim 1, wherein the pH of the suspension prior to the changing step is less than or equal to about the pKa of the ionizable molecule.

12. The method as in claim 1, wherein the pKa of the ionizable molecule is between about 6 and 7.

13. The method as in claim 1, wherein the pKa of the ionizable molecule is about 6.2.

14. The method as in claim 1, wherein the permeate flux throughout the diafiltration step is less than or equal to about 120 L/m$^2$h when the transmembrane pressure is between about 1 psi and about 20 psi, or between about 10 psi and about 15 psi.

15. The method as in claim 1, comprising incubating the ionizable molecule and the mRNA in the suspension for greater than or equal to about 1 minute.

16. The method as in claim 1, wherein the encapsulation efficiency after the incubation step is greater than or equal to about 70%.

17. The method as in claim 1, wherein the ionizable molecule comprises a nitrogen.

18. The method as in claim 1, wherein the ionizable molecule is a cationic lipid.

19. The method as in claim 18, wherein the cationic lipid is selected from the group consisting of 2,2-dilinoleyl-4- dimethylaminoethyl-[1,3]-dioxolane, dilinoleyl-methyl-4-dimethylaminobutyrate, and di((Z)-non-2-en-1-yl) 9-((4-(dimethylamino)butanoyl)oxy)heptadecanedioate.

20. The method as in claim 1, wherein the particle comprises a sterol molecule.

21. The method of claim 20, wherein the sterol molecule is a cholesterol molecule.

22. The method as in claim 1, wherein the particles in the filtered suspension have an average cross-sectional dimension less than or equal to about 150 nm.

23. The method as in claim 1, wherein the particles in the suspension have a first zeta potential and the particles in the filtered suspension have a second zeta potential, and wherein the second zeta potential is less than the first zeta potential.

24. The method as in claim 1, wherein a coefficient of variation of a cross-sectional dimension of the particles in the filtered suspension is less than or equal to about 20%.

25. The method as in claim 1, wherein the cross-sectional dimension of the particles is a largest cross-sectional dimension of the particles.

26. The method of claim 1, wherein the pH of the suspension prior to the changing step is less than or equal to about 6.5.

27. The method of claim 1, wherein the pH of the suspension after the changing step is greater than or equal to about 6.5.

28. The method of claim 1, wherein the second pH is greater than or equal to 0.5 pH units and less than or equal to about 2 pH units greater than the pKa of the ionizable molecule.

29. A method comprising:
changing a pH of a suspension comprising particles comprising mRNA comprising greater than or equal to 100 nucleotides and less than or equal to 10,000 nucleotides in length, and an ionizable molecule and a molecule capable of reducing particle aggregation from a first pH to a second pH, wherein the second pH is greater than a pKa of the ionizable molecule, wherein the pKa of the ionizable molecule is greater than or equal to about 6, and subsequently
forming a composition comprising at least a portion of the particles, wherein a coefficient of variation of a cross-sectional dimension of the particles in the composition is less than or equal to about 20%,
by filtering the suspension by tangential flow filtration (TFF) to produce a filtered suspension comprising the composition.

30. A method comprising:
changing an average zeta potential of a plurality of particles comprising mRNA comprising greater than or equal to 100 nucleotides and less than or equal to 10,000 nucleotides in length, and an ionizable molecule and a molecule capable of reducing particle aggregation in a suspension from a first zeta potential to a second zeta potential, wherein the second zeta potential is less than the first zeta potential; and subsequently
filtering the suspension by tangential flow filtration (TFF) to produce a filtered suspension comprising at least a portion of the particles, wherein a weight percentage of mRNA in the particles in the filtered suspension is greater than or equal to about 50% and less than or equal to about 99%.

31. The method as in claim 30, wherein the first zeta potential is greater than or equal to about 0 mV.

32. A method comprising:
changing an average zeta potential of a plurality of particles comprising mRNA comprising greater than or equal to 100 nucleotides and less than or equal to 10,000 nucleotides in length, and an ionizable molecule and a molecule capable of reducing particle aggregation in a suspension from a first zeta potential to a second zeta potential, wherein the second zeta potential is less than the first zeta potential; and subsequently
forming a composition comprising at least a portion of the particles, wherein a weight percentage of mRNA in the particles in the composition is greater than or equal to about 50% and less than or equal to about 99%,
by filtering the suspension by tangential flow filtration (TFF) to produce a filtered suspension comprising the composition.

* * * * *